(12) United States Patent
Aehle et al.

(10) Patent No.: US 8,546,121 B2
(45) Date of Patent: Oct. 1, 2013

(54) VARIANTS OF AN ALPHA-AMYLASE WITH IMPROVED PRODUCTION LEVELS IN FERMENTATION PROCESSES

(75) Inventors: Wolfgang Aehle, Zwingenberg (DE); Neelam S. Amin, Burlingame, CA (US)

(73) Assignee: Danisco US Inc., Palo Alto, CA (US)

( * ) Notice: Subject to any disclaimer, the term of this patent is extended or adjusted under 35 U.S.C. 154(b) by 421 days.

(21) Appl. No.: 12/601,759

(22) PCT Filed: May 29, 2008

(86) PCT No.: PCT/US2008/006787
§ 371 (c)(1),
(2), (4) Date: Oct. 14, 2010

(87) PCT Pub. No.: WO2008/153815
PCT Pub. Date: Dec. 18, 2008

(65) Prior Publication Data
US 2011/0027252 A1  Feb. 3, 2011

Related U.S. Application Data

(60) Provisional application No. 60/924,745, filed on May 30, 2007.

(51) Int. Cl.
*C12N 9/26* (2006.01)

(52) U.S. Cl.
USPC ........................................................ 435/201

(58) Field of Classification Search
None
See application file for complete search history.

(56) References Cited

U.S. PATENT DOCUMENTS

| 6,261,828 B1 | 7/2001 | Lund |
| 6,528,298 B1 | 3/2003 | Svendsen et al. |
| 6,887,986 B1 | 5/2005 | Svendsen et al. |
| 2002/0155574 A1 | 10/2002 | Thisted et al. |
| 2003/0064908 A1 | 4/2003 | Bisgard-Frantzen et al. |
| 2003/0129718 A1* | 7/2003 | Andersen et al. ............ 435/183 |

FOREIGN PATENT DOCUMENTS

| WO | WO-96/23873 | 8/1996 |
| WO | WO-99/19467 | 4/1999 |
| WO | WO-01/66712 | 9/2001 |
| WO | WO-02/24732 | 3/2002 |
| WO | WO2005108540 | * 11/2005 |
| WO | WO-2006/002643 | 1/2006 |
| WO | WO-2006/031554 | 3/2006 |
| WO | WO-2006/037484 | 4/2006 |
| WO | WO-2007/079938 | 7/2007 |

OTHER PUBLICATIONS

Wishart et al, A single mutation converts a novel phosphotyrosine binding domain into a dual-specificity phosphatase. J Biol Chem. Nov. 10, 1995;270(45):26782-26785.*
Whisstock et al, Prediction of protein function from protein sequence and structure. Q Rev Biophys. Aug. 2003;36(3):307-40. Review.*
A_Geneseq_201215 database Acc# AEE06381 from Kottwitz et al, WO2005108540 (SEQ ID No: 3). Alignment with SEQ ID No: 1 His183Asp.*
Svendsen et al, 2002 US 6,361,989 SEQ ID No: 24. Alignment with SEQ ID No: 1 with H183D substitution.*
International Search Report for PCT/US2008/006787 mailed Nov. 24, 2008, 5 pp.
Kanai, R. et al. "Biochemical and Crystallographic Analyses of Maltohexaose-Producing Amylase from Alkalophilic *Bacillus* sp. 707." *Biochemistry* 43(44): 14047-14056, Nov. 1, 2004.
Kimura, K. et al. "Cloning of a gene for maltohexaose producing amylase of an alkalophilic *Bacillus* and hyper-production of the enzyme in *Bacillus subtilis* cells." *Applied Microbiology and Biotechnology* 27(4): 372-377, Jan. 1, 1988.
Tsukamoto, A. et al. "Nucleotide sequence of the maltohexaose-producing amylase gene from an alkalophilic *Bacillus* sp. #707 and structural similarity to liquefying type alpha-amylases." Biochemical and Biophysical Research Communications 151(1): 25-31, Feb. 29, 1988.
GenBank Accession No. CAL48155, accessed at www.ncbi.nlm.nih.gov/protein/115307626?sat=13&satkey=12214009; Sep. 22, 2006; *Bacillus* sp.; Bessler, C., et al., "Alpha amylase variants having an elevated solvent stability, method for the production thereof and detergents and cleansers containing these alpha amylase variants." WO2006/037484-A; Apr. 13, 2006, Henkel Kommanditgesellschaft Auf Aktien (DE), 1 pg.
UnitProtKB/Swissprot Accession No. P19571, accessed at www.uniprot.org/uniprot/P19571; Feb. 1, 1991; *Bacillus* sp. (strain 707); Tsukamoto, A., et al., "Nucleotide sequence of the maltohexaose-producing amylase gene from an alkalophilic *Bacillus* sp. #707 and structural similarity to liquefying type alpha-amylases." Biochem. Biophys. Res. Commun. 151: 25-31 (1998), 3pp.

* cited by examiner

*Primary Examiner* — Sheridan Swope
(74) *Attorney, Agent, or Firm* — Danisco US Inc.

(57) ABSTRACT

Variants of *Bacillus* sp. no. 707 alpha amylase are provided that are produced more efficiently and thus more economically. Higher fermentation yields are achieved through introducing amino acid variations that promote solubility of the variant in a fermentation broth. Increased solubility allows more enzyme to remain in solution after expression in a host cell. This in turn increases the efficiency with which the expressed variant enzyme can be recovered from the fermentation broth.

1 Claim, 4 Drawing Sheets

FIG. 1

```
1          11         21         31         41         51
HHNGTNGTMM QYFEWYLPND GNHWNRLNSD ASNLKSKGIT AVWIPPAWKG ASQNDVGYGA
HHNGTNGTMM QYFEWYLPND GNHWNRLRSD ASNLKDKGIT AVWIPPAWKG ASQNDVGYGA 61         71         81         91         101        111
YDLYDLGEFN QKGTVRTKYG TRSQLQAAVT SLKNNGIQVY GDVVMNHKGG ADATEMVRAV
YDLYDLGEFN QKGTVRTKYG TRNQLQAAVT ALKSNGIQVY GDVVMNHKGG ADATEWVRAV 121        131        141        151        161        171
EVNPNNRNQE VTGEYTIEAW TRFDFPGRGN THSSFKWRWY HFDGVDWDQS RRLNNRIYKF
EVNPSNRNQE VSGDYTIEAW TKFDFPGRGN THSNFKWRWY HFDGVDWDQS RQLQNRIYKF 181        191        201        211        221        231
RGHGKAWDWE VDTENGNYDY LMYADIDMDH PEVVNELRNW GVWYTNTLGL DGFRIDAVKH
RGDGKGWDWE VDTENGNYDY LMYADIDMDH PEVVNELRNW GVWYTNTLGL DGFRIDAVKH 241        251        261        271        281        291
IKYSFTRDWI NHVRSATGKN MFAVAEFWKN DLGAIENYLQ KTNWNHSVFD VPLHYNLYNA
IKYSFTRDWL THVRNTTGKN MFAVAEFWKN DIGAIENYLS KTNWNHSVFD VPLHYNLYNA 301        311        321        331        341        351
SKSGGNYDMR NIFNGTVVQR HPSHAVTFVD NHDSQPEEAL ESFVEEWFKP LAYALTLTRE
SRSGGNYDMR QIFNGTVVQR HPTHAVTFVD NHDSQPEEAL ESFVEEWFKP LAYALTLTRD 361        371        381        391        401        411
QGYPSVFYGD YYGIPTHGVP AMRSKIDPIL EARQKYAYGK QNDYLDHHNI IGWTREGNTA
QGYPSVFYGD YYGIPTHGVP AMKSKIDPIL EARQKYAYGK QNDYLDHHNM IGWTREGNTA 421        431        441        451        461        471
HPNSGLATIM SDGAGGSKWM FVGRNKAGQV WSDITGNRTG TVTINADGWG NFSVNGGSVS
HPNSGLATIM SDGPGGNKWM YVGRNKAGQV WRDITGNRSG TVTINADGWG NFSVNGGSVS

481
IWVNK  Bacillus sp. no. 707 α-amylase (SEQ ID NO: 1)
IWVNN  Bacillus sp. A 7-7 (DSM 12368) α-amylase (SEQ ID NO: 2)
```

Figure 2 *Results of SIM with:* Sequence 1: *Bacillus* sp. no. 707, (485 residues)
Sequence 2: *Bacillus* sp. no. 7-7, (484 residues)

*Using the parameters:* Comparison matrix: BLOSUM62, Number of alignments computed: 20, Gap open penalty: 12, Gap extension penalty: 4

93.4% identity in 484 residues overlap; Score: 2567.0; Gap frequency: 0.0%

```
707,   1 HHNGTNGTMMQYFEWYLPNDGNHWNRLNSDASNLKSKGITAVWIPPAWKGASQNDVGYGA
7-7,   1 HHNGTNGTMMQYFEWYLPNDGNHWNRLRSDASNLKDKGITAVWIPPAWKGASQNDVGYGA
         *************************** ****** ************************

707,  61 YDLYDLGEFNQKGTVRTKYGTRSQLQAAVTSLKNNGIQVYGDVVMNHKGGADATEMVRAV
7-7,  61 YDLYDLGEFNQKGTVRTKYGTRNQLQAAVTALKSNGIQVYGDVVMNHKGGADATEWVRAV
         ********************** ******* ** ********************* ****

707, 121 EVNPNNRNQEVTGEYTIEAWTRFDFPGRGNTHSSFKWRWYHFDGVDWDQSRRLNNRIYKF
7-7, 121 EVNPSNRNQEVSGDYTIEAWTKFDFPGRGNTHSNFKWRWYHFDGVDWDQSRQLQNRIYKF
         **** ****** * ******* *********** **************** * ******

707, 181 RGHGKAWDWEVDTENGNYDYLMYADIDMDHPEVVNELRNWGVWYTNTLGLDGFRIDAVKH
7-7, 181 RGDGKGWDWEVDTENGNYDYLMYADIDMDHPEVVNELRNWGVWYTNTLGLDGFRIDAVKH
         ** ** ******************************************************

707, 241 IKYSFTRDWINHVRSATGKNMFAVAEFWKNDLGAIENYLQKTNWNHSVFDVPLHYNLYNA
7-7, 241 IKYSFTRDWLTHVRNTTGKNMFAVAEFWKNDIGAIENYLSKTNWNHSVFDVPLHYNLYNA
         ********* *** * ************** ******* ********************

707, 301 SKSGGNYDMRNIFNGTVVQRHPSHAVTFVDNHDSQPEEALESFVEEWFKPLAYALTLTRE
7-7, 301 SRSGGNYDMRQIFNGTVVQRHPTHAVTFVDNHDSQPEEALESFVEEWFKPLAYALTLTRD
         * ******** *********** *************************************

707, 361 QGYPSVFYGDYYGIPTHGVPAMRSKIDPILEARQKYAYGKQNDYLDHHNIIGWTREGNTA
7-7, 361 QGYPSVFYGDYYGIPTHGVPAMKSKIDPILEARQKYAYGKQNDYLDHHNMIGWTREGNTA
         ********************** ************************* **********

707, 421 HPNSGLATIMSDGAGGSKWMFVGRNKAGQVWSDITGNRTGTVTINADGWGNFSVNGGSVS
7-7, 421 HPNSGLATIMSDGPGGNKWMYVGRNKAGQVWRDITGNRSGTVTINADGWGNFSVNGGSVS
         ************* *** *** ********* ***** **********************

707, 481 IWVN
7-7, 481 IWVN
         ****
```

Amylase activity of 707 amylase compared to 707 amylase variants (R172Q, H183D, S255N, and S36D/S255N) grown in shake flasks expressed in arbitrary units. The # symbol represents the clone number assayed.

VARIANTS OF AN ALPHA-AMYLASE WITH IMPROVED PRODUCTION LEVELS IN FERMENTATION PROCESSES

SEQUENCE LISTING

Also attached is a sequence listing comprising SEQ ID NOS: 1-26, which are herein incorporated by reference in their entirety.

FIELD OF THE INVENTION

Disclosed are nucleic acids encoding polypeptides with amylase activity, wherein the polypeptide is modified from a *Bacillus* α-amylase, particularly *Bacillus* sp. no. 707 α-amylase.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing the same α-1,4-linked glucose units, as well as α-1,6 branch points every 24-30 glucose units; its MW may be as high as 100 million.

Sugars from starch, in the form of concentrated dextrose syrups, are currently produced by an enzyme catalyzed process involving: (1) liquefaction (or thinning) of solid starch with an α-amylase into dextrins having an average degree of polymerization of about 7-10, and (2) saccharification of the resulting liquefied starch, i.e., starch hydrolysate, with amyloglucosidase (also called glucoamylase). The resulting syrup has a high glucose content. Much of the glucose syrup that is commercially produced is subsequently enzymatically isomerized to a dextrose/fructose mixture known as isosyrup.

α-Amylases (EC 3.2.1.1) hydrolyze starch, glycogen, and related polysaccharides by cleaving internal α-1,4-glucosidic bonds at random. These enzymes have a number of important commercial applications, including starch liquefaction, textile desizing, starch modification in the paper and pulp industry, grain processing, backing and brewing. α-Amylases also can be used in automatic dishwashing detergent and laundry detergent formulations, including those containing bleach, to remove starchy stains during washing. The α-amylase from *Bacillus* sp. no. 707 shows particularly advantageous performance when used in these applications. Unfortunately, this α-amylase is not expressed at high levels, complicating its economical manufacture and commercial use.

α-Amylases are isolated from a wide variety of bacterial, fungal, plant and animal sources. Many industrially important α-amylases are isolated from *Bacillus* sp., in part because of the generally high capacity of *Bacillus* to secrete amylases into the growth medium. *Bacillus* sp. A 7-7 (DSM 12368), for instance, secretes α-amylase at advantageously high levels. Although the *Bacillus* sp. A 7-7 α-amylase can be produced economically, the enzyme does not perform as well as the α-amylase from *Bacillus* sp. no. 707. Accordingly, there is a need in the art to express the better performing variant of *Bacillus* sp. no. 707 α-amylase at production levels comparable to, for example, the *Bacillus* sp. A 7-7 α-amylase. Such a variant would be useful in more effective and economical detergent formulations or other formulations.

SUMMARY

Variants of α-amylase are provided that are produced more efficiently and thus more economically. Higher fermentation yields are achieved through introducing amino acid variations that promote solubility of the variant in a fermentation broth. That is, increased solubility allows more enzyme to remain in solution after expression in a host cell. This in turn increases the efficiency with which the expressed variant enzyme can be recovered from the fermentation broth.

In one embodiment, the primary structure of the variant is modified to resemble an α-amylase that is soluble at high concentrations in a fermentation broth. The variant may be a high-performance *Bacillus* sp. no. 707 α-amylase that advantageously can be expressed more economically for use in cleaning formulations and the like. Suitable variants include those with fewer hydrophobic amino acid residues on the enzyme surface, which promote aggregation and precipitation of the enzyme in an aqueous solution.

Accordingly, an object is to provide an isolated variant of a wild-type first α-amylase and an encoding nucleic acid, where
(a) the α-amylase variant comprises at least one modified amino acid compared to the wild-type first α-amylase;
(b) the α-amylase variant exhibits α-amylase activity; and
(c) the at least one modified amino acid is the same as an amino acid found in a corresponding position of an amino acid sequence of a second α-amylase,
where the second α-amylase has a greater solubility than the wild-type first α-amylase, and where the amino acid sequence of the variant α-amylase is different by at least one amino acid from the second α-amylase. In one embodiment, the α-amylase variant is capable of being expressed at a higher level in a host cell, compared to a level of expression of the wild-type first α-amylase.

The α-amylase variant may comprise 1, 2, 3, 4, 5, 6, 7, 8, 9, 10, 11, 12, 13, 14, 15, 20, 25, 30, 35, or 40 amino acid modifications, e.g., 1, 2, 3, 4, 5, 6, 7, 8, 9, 10, or more amino acids. The amino acid sequences of the first wild-type α-amylase and the second α-amylase may share at least 60%, 80%, or 90% sequence identity. In one embodiment, the wild-type first α-amylase and the second α-amylase are bacterial α-amylases, e.g., *Bacillus* α-amylases. As a non-limiting example, the wild-type first α-amylase may be a *Bacillus* sp. no. 707 α-amylase [Tsukamoto, A., Kimura, K., Ishii, Y., Takano, T. and Yamane, K. (1988) Nucleotide sequence of the maltohexaose-producing amylase gene from an alkalophilic *Bacillus* sp. #707 and structural similarity to liquefying type alpha-amylases Biochem. Biophys. Res. Commun. 151 (1), 25-31] comprising the amino acid sequence set forth in SEQ ID NO:1 and/or the second α-amylase may be a *Bacillus* sp. A 7-7 (DSM 12368) α-amylase [Bessler, C., Wieland, S. and Maurer, K. H. Alpha amylase variants having an elevated solvent stability, method for the production thereof and detergents and cleansers containing these alpha amylase variants. Patent: WO 2006037484-A 13 Apr. 2006; HENKEL KOMMANDITGESELLSCHAFT AUF AKTIEN (DE)] comprising the amino acid sequences set forth SEQ ID NO:2 or SEQ ID NO:3 or SEQ ID NO:7 or SEQ ID NO:8. The modified amino acid of the α-amylase variant may be selected from the group consisting of N28R, S36D, S83N, M116W, R142K, R172Q, H183D, A186G, N251T, S255N, A256T, F441Y, S452R and K485N, e.g., N28R, S36D, M116W, R172Q, H183D, S255N and A256T.

An object is also to provide an isolated host cell comprising the encoding nucleic acid above, a vector operably linked to the isolated nucleic acid above, and an isolated host cell comprising the same vector. The isolated host cell may be a microorganism, e.g., a bacterium or a fungus. Suitable host cells may be selected from the group consisting of *Bacillus subtilis, B. licheniformis, B. lentus, B. brevis, B. stearother-* mophilus, B. alkalophilus, B. amyloliquefaciens, B. coagulans, B. circulans, B. lautus, B. thuringiensis, Streptomyces lividans, or S. murinus; or a Gram negative bacterium, wherein said Gram negative bacterium is Escherichia coli or a Pseudomonas species.

Another object is to provide a detergent additive comprising the α-amylase variant above. The detergent additive may be in the form of a non-dusting granulate, microgranulate, stabilized liquid, or protected enzyme. The detergent additive further may comprise an enzyme selected from the group consisting of a cellulase, protease, aminopeptidase, amylase, carbohydrase, carboxypeptidase, catalase, chitinase, cutinase, cyclodextrin glucanotransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, xylanase, pullulanase, isoamylase, carrageenase, or any combination thereof. In particular, the amylase may be another α-amylase, a β-amylase, an isoamylase, or a glucoamylase.

A detergent composition is provided that comprises the detergent additive above. The detergent composition further may comprise an enzyme from the group consisting of a cellulase, protease, aminopeptidase, amylase, carbohydrase, carboxypeptidase, catalase, chitinase, cutinase, cyclodextrin glucanotransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, xylanase, pullulanase, isoamylase, carrageenase, or any combination thereof.

Another object is to provide a manual or automatic dishwashing composition comprising the α-amylase variant above. The composition further may comprise one or more of a surfactant, detergent builder, complexing agent, polymer, bleaching system, stabilizer, foam booster, suds suppressor, anti-corrosion agent, soil-suspending agent, anti-soil redeposition agent, dye, bactericide, hydrotope, tarnish inhibitor, and perfume. The composition further may comprise an enzyme selected from the group consisting of a cellulase, protease, aminopeptidase, amylase, carbohydrase, carboxypeptidase, catalase, chitinase, cutinase, cyclodextrin glucanotransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, xylanase, pullulanase, isoamylase, carrageenase, or any combination thereof. A method of cleaning dishes comprises administering the manual or automatic dishwashing composition above.

Yet another object is to provide a laundry detergent additive comprising the α-amylase variant above. A laundry detergent composition may comprise the laundry additive and further may comprise one or more of a surfactant, detergent builder, complexing agent, polymer, bleaching system, stabilizer, foam booster, suds suppressor, anti-corrosion agent, soil-suspending agent, anti-soil redeposition agent, dye, bactericide, hydrotope, optical brightener, fabric conditioner, and perfume. A method of laundering comprises administering the laundry detergent additive above.

Another object is to provide a biofilm-hydrolyzing composition comprising the α-amylase variant above. The biofilm hydrolyzing composition may be in the form of a solution, powder, paste, gel, liquid, ointment, tablet or gel. The composition further may comprise a cellulase, hemicellulase, xylanase, lipase, protease, pectinase, antimicrobial agent, or any combination thereof. A method of hydrolyzing a biofilm comprises administering the composition above for a time sufficient to hydrolyze the biofilm.

Another object is to provide a starch processing composition comprising the α-amylase variant above in an aqueous solution. The starch processing composition further may comprise a glucoamylase, isoamylase, pullulanase, phytase or a combination thereof. A method of processing a starch comprises administering the composition for a time sufficient to process the starch.

Another object is to provide a composition for saccharifying starch comprising the α-amylase variant above in a solution. A method of saccharifying starch comprises administering the composition for a period sufficient to saccharify the starch. A further object is to provide a composition for liquefying starch comprising the α-amylase variant above in a solution. A method of liquefying starch comprises administering the composition for a period sufficient to liquefy the starch.

Yet another object is to provide a textile desizing composition comprising the α-amylase variant above in a solution. The textile desizing composition further may comprise another enzyme. A method of desizing a textile comprises administering the textile desizing composition for a time sufficient to desize the textile.

Another object is to provide a baking composition comprising the α-amylase variant above in a solution or gel. A method of baking comprises administering the baking composition.

BRIEF DESCRIPTION OF THE DRAWINGS

The accompanying drawings are incorporated in and constitute a part of this specification and illustrate various embodiments. In the drawings:

FIG. 1 depicts an amino acid sequence alignment between the mature forms of Bacillus subtilus sp. no. 707 α-amylase (SEQ ID NO:1) (Swissprot Accession No. P 19571) and Bacillus sp. A 7-7 α-amylase (SEQ ID NO:2). Highlighted residues are different in the two amino acid sequences.

FIG. 2 depicts an SIM amino acid sequence alignment (Xiaoquin Huang and Webb Miller. (1991) A Time-Efficient, Linear-Space Local Similarity Algorithm. Advances in Applied Mathematics, vol. 12, pp. 337-357) between the mature forms of Bacillus subtilus sp. no. 707 α-amylase (SEQ ID NO:1) (Swissprot Accession No. P 19571) and Bacillus sp. A 7-7 (DSM 12368) α-amylase (SEQ ID NO:7) (GenBank Accession No. CAL48155). The identical amino acid positions are marked by an asterisk below the sequence alignment.

DETAILED DESCRIPTION

Figure 3:
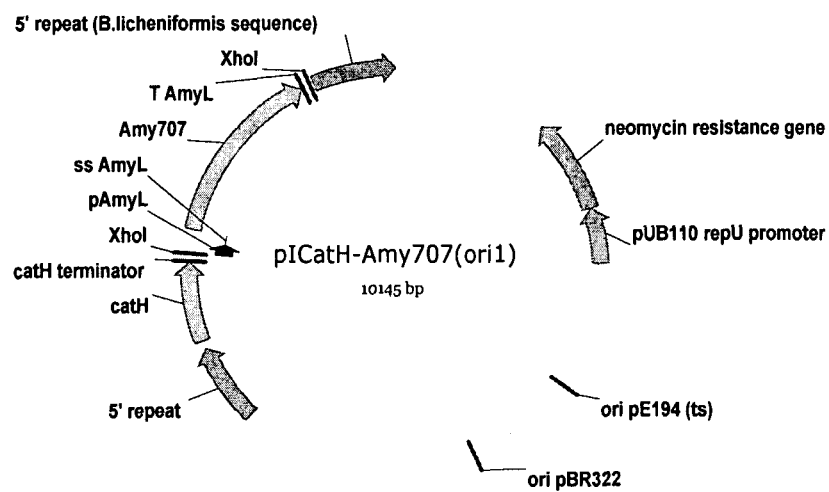
FIG. 3 shows the diagram for plasmid pICatH-Amy707 used for the expression of Bacillus sp. no. 707 amylase variants. pICatH contains the following features: a temperature sensitive origin of replication (ori pE194, for replication in Bacillus), replication ori from pBR322 (for amplification in E. coli), a neomycin resistance gene for selection, and the native B. licheniformis chloramphenicol resistance gene (CAT) for chloramphenicol antibiotic selection, chromosomal integration and cassette amplification.

Variants of α-amylase are provided that are produced more efficiently and thus more economically by modifying amino acid residues important to the solubility of the enzyme. For example, variants of *Bacillus* sp. no. 707 α-amylase are provided that are more soluble than the wild-type *Bacillus* sp. no. 707 α-amylase in a fermentation broth of a host cell expressing the variant. The variants additionally may have a higher solubility in the expression host cell, e.g., in the host cell cytoplasm. Since the *Bacillus* sp. no. 707 α-amylase variants have greater solubility, the variants can be isolated and purified more efficiently from a fermentation broth, for example, and formulations comprising the variants thus can be produced more economically.

Formulations comprising the present *Bacillus* sp. no. 707 α-amylase variants include cleaning formulations (e.g., automatic dishwashing detergent and laundry detergent formulations), biofilm treating formulations, starch processing formulations, textile desizing formulations, baking formulations, and the like. The following details how this can be done and provides compositions and uses for the α-amylase variants produced thereby.

1. Definitions & Abbreviations

In accordance with this detailed description, the following abbreviations and definitions apply. It must be noted that as used herein, the singular forms "a," "an," and "the" include plural referents unless the context clearly dictates otherwise. Thus, for example, reference to "an enzyme" includes a plurality of such enzymes and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1 Definitions

"Amylase" means an enzyme that is, among other things, capable of catalyzing the degradation of starch. "Amylase" includes any amylase, such as glucoamylases, α-amylase, β-amylases, and wild-type α-amylases of *Bacillus* sp., such as *B. licheniformis* and *B. subtilis*. Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from starch.

"α-Amylase variant," "α-amylase variant polypeptide," and "variant enzyme" mean an α-amylase protein that has an amino acid sequence that has been modified from the amino acid sequence of a wild-type α-amylase. As used herein, "parent enzymes," "parent sequence," "parent polypeptide," "wild-type α-amylase protein," and "parent polypeptides" mean enzymes and polypeptides from which the α-amylase variant polypeptides are based, e.g., a *Bacillus* sp. no. 707 α-amylase. A wild-type α-amylase occurs naturally. "α-Amylase variants" differ from a wild-type α-amylase in the amino acid residues of the mature protein, i.e., the protein sequence without a signal sequence. The α-amylase variant can be a fusion protein comprises a mature or variant *Bacillus* sp. no. 707 α-amylase linked to a signal peptide, for example, from another α-amylase. The term "variant" may be used interchangeably with the term "mutant."

"Variants" refer to polypeptides and nucleic acids. Variants include insertions, substitutions, transversions, truncations, and/or inversions at one or more locations in the amino acid or nucleotide sequence, respectively. Variant nucleic acids can include sequences that are complementary to sequences that are capable of hybridizing to the nucleotide sequences presented herein. For example, a variant sequence is complementary to sequences capable of hybridizing under stringent conditions, e.g., 50° C. and 0.2×SSC (1×SSC=0.15 M NaCl, 0.015 M $Na_3$ citrate, pH 7.0), to the nucleotide sequences presented herein. More particularly, the term variant encompasses sequences that are complementary to sequences that are capable of hybridizing under highly stringent conditions, e.g., 65° C. and 0.1×SSC, to the nucleotide sequences presented herein.

"Isolated" means that the sequence is at least substantially free from at least one other component that the sequence is naturally associated and found in nature.

"Purified" means that the material is in a relatively pure state, e.g., at least about 90% pure, at least about 95% pure, or at least about 98% pure.

"Thermostable" means the enzyme is more thermostable than a reference enzyme. In the present application, an α-amylase variant is more thermostable than a wild-type *Bacillus* sp. no. 707 α-amylase α-amylase if the variant has a relatively higher enzymatic activity after a specific interval of time under the same experimental conditions, e.g., the same temperature, substrate concentration, etc. Alternatively, a more thermostable enzyme has a higher heat capacity determined by differential scanning calorimetry, compared to a reference enzyme.

"pH range" means the pH values over which an enzyme exhibits activity.

As used herein, "pH stable" means the enzyme is more stable than a reference enzyme at a particular pH. In the present application, an α-amylase variant is more pH stable than a wild-type *Bacillus* sp. no. 707 α-amylase if the variant has a relatively higher activity after a specific interval of time under the same experimental conditions, e.g., the same pH, etc.

As used herein, "food" includes both prepared food, as well as an ingredient for a food, such as flour.

As used herein, "food ingredient" includes a formulation that is or can be added to a functional food or foodstuff and includes formulations used at low levels in a wide variety of products that require, for example, acidifying or emulsifying. The food ingredient may be in the form of a solution or as a solid, depending on the use and/or the mode of application and/or the mode of administration.

As used herein, "functional food" means food capable of providing not only a nutritional effect and/or a taste satisfaction, but also any further beneficial effect to the consumer.

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA. Synthesis of nucleotide sequences is well known in the art (See e.g., Beaucage and Caruthers, Tetrahedron Lett., 22:1859-1862 [1981]), including the use of automated synthesizers (See e.g., Needham-VanDevanter et al., Nucl. Acids Res., 12:6159-6168 [1984]). DNA sequences can also be custom made and ordered from a variety of commercial sources.

"Homologue" means an entity having a certain degree of identity or "homology" with the subject amino acid sequences and the subject nucleotide sequences. A "homologous sequence" includes an amino acid sequence at least 75%, 80%, 85% or 90% identical, particularly at least 95%, 96%, 97%, 98% or 99% identical to the subject sequence. Typically, homologues will comprise the same active site residues as the subject amino acid sequence.

As used herein, "hybridization" includes the process by which a strand of nucleic acid joins with a complementary strand through base pairing, as well as the process of amplification as carried out in polymerase chain reaction (PCR) technologies. The α-amylase variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The α-amylase variant nucleic acid may be codon-optimized to further increase expression.

As used herein, a "synthetic" compound is produced by in vitro chemical or enzymatic synthesis. It includes, but is not limited to, α-amylase variant nucleic acids made with optimal codon usage for host organisms, such as the methylotrophic yeasts *Pichia*, *Hansenula*, *Streptomyces*, and *Trichoderma*, e.g., *T. reesei*, or other expression hosts of choice.

As used herein, "transformed cell" includes cells that have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, "biologically active" refers to a sequence having a similar structural, regulatory or biochemical function as the naturally occurring sequence, although not necessarily to the same degree.

"Solubility" relates to the quantity of a particular substance that can dissolve in a particular solvent. A protein that is more soluble than another can reach a higher concentration in the solvent without precipitating out of solution. A solvent for this purpose includes any millieu in which the protein may occur, such as an aqueous buffer or salt solution, a fermentation broth, or the cytoplasm of an expression host.

1.2 Abbreviations

The following abbreviations apply unless indicated otherwise:

| | |
|---|---|
| 3D | three dimensional |
| AE | alcohol ethoxylate |
| AEO | alcohol ethoxylate |
| AEOS | alcohol ethoxysulfate |
| AES | alcohol ethoxysulfate |
| AFAU | acid fungal α-amylase units |
| AGU | glucoamylase activity unit |
| AOS | α-olefinsulfonate |
| AS | alcohol sulfate |
| BAA | bacterial α-amylase |
| cDNA | complementary DNA |
| CMC | carboxymethylcellulose |
| DE | Dextrose Equivalent |
| DNA | deoxyribonucleic acid |
| DP3 | degree of polymerization with three subunits |
| DPn | degree of polymerization with n subunits |
| DS | dry solid |
| DTMPA | diethyltriaminopentaacetic acid |
| EC | enzyme commission for enzyme classification |
| EDTA | ethylenediaminetetraacetic acid |
| EDTMPA | ethylenediaminetetramethylene phosphonic acid |
| EO | ethylene oxide |
| EP | expressed protein |
| F&HC | fabric and household care |
| HFCS | high fructose corn syrup |
| HFSS | high fructose starch based syrup |
| IPTG | isopropyl β-D-thiogalactoside |
| LAS | linear alkylbenezenesulfonate |
| LAT | *B. licheniformis* α-amylase |
| LU | Lipase Units |
| MW | molecular weight |
| nm | nanometer |
| NOBS | nonanoyloxybenzenesulfonate |
| NTA | nitrilotriacetic acid |
| PCR | polymerase chain reaction |
| PEG | polyethyleneglycol |
| pI | isoelectric point |
| ppm | parts per million |
| PVA | poly(vinyl alcohol) |
| PVP | poly(vinylpyrrolidone) |
| RAU | Reference Amylase Units |
| RMS | root mean square |
| RNA | ribonucleic acid |
| SAS | secondary alkane sulfonates |
| 1X SSC | 0.15 M NaCl, 0.015 M Na$_3$ citrate, pH 7.0 |
| SSF | simultaneous saccharification and fermentation |
| TAED | tetraacetylethylenediamine |
| TNBS | trinitrobenzenesulfonic acid |
| w/v | weight/volume |
| w/w | weight/weight |
| wt | wild-type |
| µL | microliter |

2. α-Amylase Variants

The α-amylase variants herein are created from a wild-type α-amylase, e.g., a *Bacillus* sp. no. 707 α-amylase. The present variants have one or more modifications to the amino acid sequence that affect production levels relative to a wild-type α-amylase, such as by increasing the solubility of the variant in a fermentation broth of a host cell expressing the variant. In this manner, a variant can combine the high performance characteristic of an α-amylase from *Bacillus* sp. no. 707, for example, with the high production levels of an α-amylase of other species or strain. In one embodiment, high production levels are conferred by amino acid variations that improve the aqueous solubility of the α-amylase variant.

For the purpose of this disclosure, an amino acid substitution may be designated R172Q, for example, meaning that an arginine (R) residue at position 172 is replaced with a glutamine (Q) residue, where the amino acids are designated by single letter abbreviations commonly known in the art. The residue position number is the same as used in the *Bacillus* sp. no. 707 α-amylase shown as the top sequence in FIG. 1 (SEQ ID NO:1).

Without being limited by theory, the level of α-amylase expression is believed due in part to the primary sequence of the α-amylase. For instance, specific amino acid residues may promote aggregation and precipitation of the expressed enzyme, lowering the amount of enzyme that is recoverable from a fermentation broth. Systematic variation of the primary sequence of the enzyme through genetic engineering can identify specific amino acid residues that contribute to the level of expression of the α-amylase. The primary sequence of an α-amylase that is expressed at high levels can guide the choice of appropriate amino acid sequence modifications. For example, the primary sequence of the *Bacillus* sp. no. 707 α-amylase differs by 33 amino acids from the primary sequence of the highly expressed α-amylase from *Bacillus* sp. A 7-7 (DSM 12368). For the purpose of this disclosure, "*Bacillus* sp. A 7-7 (DSM 12368)" is synonymous with "*Bacillus* sp. A 7-7." One or more of these 33 amino acids is believed to affect the expression level through affecting aggregation and precipitation of the expressed α-amylase. Accordingly, one or more of these 33 amino acids in the *Bacillus* sp. no. 707 α-amylase sequence can be substituted so that the variant will contain one or more amino acids corresponding to the sequence of the highly expressed *Bacillus* sp. A 7-7 α-amylase. It is expected that such a variant will be expressed at a higher level.

Alternatively, amino acids that contribute to expression levels may be identified by substituting one or more amino acids in the *Bacillus* sp. A 7-7 α-amylase sequence to correspond to the sequence of the more poorly expressed *Bacillus* sp. no. 707 α-amylase. In this case, the variant is expected to be expressed at a lower level if the substitution affects expression.

Again without being limited by theory, it is generally expected that amino acid residues that contribute to the aggregation and precipitation of the enzyme are exposed on the enzyme surface. In particular, it is expected that hydrophobic areas on the protein surface induce the aggregation process. 3D (three dimensional) structural modeling can identify those substitutions, e.g., to amino acids on the protein surface, most likely to affect expression. Amino acid substitutions can be evaluated individually or in groups of two or more. A combinatorial library, made by methods known in the art, can be used to create variants having multiple amino acid substitutions.

The present variants differ from the wild-type α-amylase sequence by the substitution, addition, or deletion of one or more amino acids. For example, a variant α-amylase may comprise 1, 2, 3, 4, 5, 6, 7, 8, 9, 10, 11, 12, 13, 14, 15, 20, 25, 30, 35, or 40 amino acid modifications, while retaining α-amylase activity. For example, a variant of *Bacillus* sp. no. 707 α-amylase can possess one or more amino acid substitutions at any of the aforementioned 33 amino acid positions, so that its sequence more closely resembles the *Bacillus* sp. A 7-7 α-amylase sequence. In one embodiment, a "variant" specifically excludes a sequence that differs from a wild-type sequence only in the first amino acid residue of the mature protein.

The primary sequence of any highly expressed α-amylase can guide the choice of amino acid sequence modifications that yield high-expression variants. For this purpose, an α-amylase with high sequence identity with a *Bacillus* sp. no. 707 α-amylase is particularly suitable because a minimal number of residues can be tested to determine which residue(s) affect expression. A *Bacillus* sp. A 7-7 α-amylase, for example, shares about a 93% sequence identity with the *Bacillus* sp. no. 707 α-amylase. A suitable *Bacillus* sp. A 7-7 α-amylase is disclosed in FIG. 1 (SEQ ID NO:2; GenBank Accession No. CAL48155). Another suitable *Bacillus* sp. A 7-7 α-amylase (SEQ ID NO:3; GenBank Accession No. CAD26710) differs by two residues, D236G and Y353C, from the *Bacillus* sp. A 7-7 α-amylase sequence shown in SEQ ID NO:2. Other suitable α-amylases include any α-amylases that are expressed at higher levels than the *Bacillus* sp. no. 707 α-amylase, particularly those α-amylases that share relatively high sequence identity with *Bacillus* sp. no. 707 α-amylase. The variant will not be identical in amino acid sequence as the highly expressed α-amylase, but will differ from this sequence by at least one amino acid. Amino acid substitutions include, but are not limited to, N28R, S36D, S83N, S91A, N94S, M116W, N125S, T132S, E134D, R142K, S154N, R172Q, N174Q, H183D, A186G, I250L, N251T, S255N, A256T, L272I, Q280S, K302R, N311 Q, S323T, E360D, R383K, I410M, A434P, S437N, F441Y, S452R, T459S, and K485N. Not all of these substitutions will confer equally useful properties. For example, the substitutions A186G and A434P advantageously reduce hydrophobicity but also are expected to destabilize the variant. Similarly, the I250L substitution is made to an amino acid that is not exposed to solvent; therefore, this substitution is expected to affect stability with little or no effect on solubility. Additional substitutions may be made to the same residue. For example, S452K, S452N, or S452D may produce better results than S452R. Various amino acid substitutions are set forth at Table 1, infra.

2.1 α-Amylase Variant Characterization

Enzyme variants can be characterized by their nucleic acid and primary polypeptide sequences, by 3D structural modeling, and/or by their specific activity. Additional characteristics of the α-amylase variant include stability, calcium ion ($Ca^{2+}$) dependence, pH range, oxidation stability, and thermostability. In one aspect, the α-amylase variants are expressed at higher levels than the wild-type α-amylase, while retaining the performance characteristics of the wild-type α-amylase. Levels of expression and enzyme activity can be assessed using standard assays known to the artisan skilled in this field. In another aspect, variants demonstrate improved performance characteristics relative to the wild-type enzyme, such as improved stability at high temperatures (i.e., 70-120° C.), and/or pH extremes (i.e., pH 4.0 to 6.0 or pH 8.0 to 11.0), and/or calcium concentrations below 60 ppm.

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant enzyme.

Altered $Ca^{2+}$ stability means the stability of the enzyme under $Ca^{2+}$ depletion has been altered i.e., increased or decreased. Mutations of importance include those that alter $Ca^{2+}$ stability, in particular improved $Ca^{2+}$ stability at high pH, i.e., pH 8.0 to 10.5.

In a further aspect, important mutations exhibit altered specific activity, especially at temperatures from 10-60° C., particularly 20-50° C., and more particularly 30-40° C., for use in cleaning compositions. For baking products, important mutations may exhibit altered specific activity at higher temperature ranges.

α-Amylase variants also may have altered oxidation stability, in particular higher oxidation stability, in comparison to the parent α-amylase. For example, increased oxidation stability is advantageous in detergent compositions, and decreased oxidation stability may be advantageous in composition for starch liquefaction.

The variant α-amylase may be more thermostable than the wild-type α-amylase. Such α-amylase variants are advantageous for use in baking or other processes that require elevated temperatures. For example, a thermostable α-amylase variant can degrade starch at temperatures of about 55° C. to about 80° C. or more. A thermostable α-amylase variant may retain its activity after exposure to temperatures of up to about 95° C.

The α-amylase variant polypeptides described herein can also have mutations that extend half-life relative to the parent enzyme by 10%, 20%, 30%, 40%, 50%, 60%, 70%, 80%, 90%, 100%, 200% or more, particularly at elevated temperatures of about 55° C. to about 95° C. or more, particularly at about 80° C. In one embodiment, the α-amylase variant can be heated for about 1-10 minutes at 80° C. or higher.

The α-amylase variants may have exo-specificity, measured by exo-specificity indices described herein, for example. α-Amylase variants include those having higher or increased exo-specificity compared to the parent enzymes or polypeptides from which they were derived, optionally when measured under identical conditions. Thus, for example, the α-amylase variant polypeptides may have an exo-specificity index 10%, 20%, 30%, 40%, 50%, 60%, 70%, 80%, 90%, 100%, 150%, 200%, 500%, 1000%, 5000%, 10,000% or higher compared to their parent polypeptides.

In one aspect, the α-amylase variant polypeptide encoded by the nucleic acid has the same pH stability as the parental sequence. In another aspect, the variant comprises a mutation that confers a greater pH stability range or shifts the pH range to a desired area for the end commercial purpose of the enzyme. For example, in one embodiment, the variant can degrade starch at about pH 5.0 to about pH 10.5. The α-amylase variant polypeptide may have a longer half-life or higher activity (depending on the assay) compared to the parent polypeptide under identical conditions, or the α-amylase variant may have the same activity as the parent polypeptide. The α-amylase variant polypeptide also may have about 10%, 20%, 30%, 40%, 50%, 60%, 70%, 80%, 90%, 100%, 200% or longer half-life compared to their parent polypeptide under identical pH conditions. Alternatively, or in addition, the enzyme variant may have higher specific activity compared to the parent polypeptide under identical pH conditions.

In another aspect, a nucleic acid complementary to a nucleic acid encoding any of the α-amylase variants set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as the methylotrophic yeasts *Pichia* and *Hansenula*.

3. Production of α-Amylase Variants

A DNA sequence encoding the enzyme variant produced by methods described herein, or by any alternative methods known in the art, can be expressed, in enzyme form, using an expression vector which typically includes control sequences encoding a suitable promoter, operator, ribosome binding site, translation initiation signal, and, optionally, a repressor gene or various activator genes.

3.1 Vectors

The recombinant expression vector carrying the DNA sequence encoding an α-amylase variant may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into a host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation of an essential metabolic pathway gene.

An expression vector typically includes the components of a cloning vector, e.g., an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. In one aspect, all the signal sequences used target the material to the cell culture media for easier enzyme collection and optionally purification. The procedures used to ligate the DNA construct encoding an α-amylase variant, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, $2^{nd}$ ed., Cold Spring Harbor, 1989 and $3^{rd}$ ed., 2001).

In the vector, the DNA sequence should be operably connected to a suitable promoter sequence. The promoter may be any DNA sequence that shows transcriptional activity in the host cell of choice and may be derived from genes encoding proteins either homologous or heterologous to the host cell. Examples of suitable promoters for directing the transcription of the DNA sequence encoding an α-amylase variant, especially in a bacterial host, are the promoter of the lac operon of *E. coli*, the *Streptomyces coelicolor* agarase gene dagA or celA promoters, various *Bacillus*-derived promoters, such as the promoters of the *Bacillus licheniformis*, *Bacillus* sp. no. 707, or *Bacillus* sp. A 7-7 α-amylase gene (amyL), the promoters of the *Bacillus stearothermophilus* maltogenic amylase gene (amyM), the promoters of the *Bacillus amyloliquefaciens* α-amylase (amyQ), and the promoters of the *Bacillus subtilis* xylA and xylB genes, etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When the gene encoding the α-amylase variant polypeptide is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. For expression in *Trichoderma reesei*, the CBHII promoter also may be used.

The expression vector may also comprise a suitable transcription terminator and, in eukaryotes, polyadenylation sequences operably connected to the DNA sequence encoding the α-amylase variant. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1, pICatH, and pIJ702.

The vector may also comprise a selectable marker, e.g., a gene the product of which complements a defect in the host cell, such as the dal genes from *B. subtilis* or *B. licheniformis*, or a gene which confers antibiotic resistance, e.g., ampicillin, kanamycin, chloramphenicol or tetracyclin resistance. Furthermore, the vector may comprise *Aspergillus* selection markers such as amdS, argB, niaD, and xxsC, a marker giving rise to hygromycin resistance, or the selection may be accomplished by co-transformation as known in the art. See, e.g., WO 91/17243.

3.2 Variant Expression and Host Organisms

While intracellular expression or solid state fermentation may be advantageous in some respects, e.g., when using certain bacteria or fungi as host cells, it is generally advantageous if the expression of the variant is extracellular and into the culture medium. In general, the *Bacillus* α-amylases mentioned herein comprise a signal sequence that permits secretion of the expressed protease into the culture medium. If desirable, this signal sequence may be replaced by a different signal sequence, which is conveniently accomplished by substitution of the DNA sequences encoding the respective signal sequence. The signal sequences are typically characterized as having three domains, an N-terminal domain, a H-domain, and a C-terminal domain and range from 18 to 35 residues in length.

The mature protein can be in the form initially of a fusion protein to a pre-protein derived from another *Bacillus* sp. or from the same species as the parental sequence. To secrete proteins in a *B. licheniformis* host cell, for example, the signal peptide of *B. licheniformis* α-amylase is frequently used; however, signal proteins from other *Bacillus* α-amylases can also be substituted. Useful signal peptides include those from *Bacillus* sp. no. 707 or *Bacillus* sp. A 7-7, for example.

An isolated cell, either comprising a DNA construct or an expression vector, is advantageously used as a host cell in the recombinant production of an α-amylase variant. The cell may be transformed with the DNA construct encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae, including *B. subtilis, B. licheniformis, B. lentus, B. brevis, B. stearothermophilus, B. alkalophilus, B. amyloliquefaciens, B. coagulans, B. lautus, B. megaterium*, and *B. thuringiensis; Streptomyces* sp., such as *S. murinus*; lactic acid bacterial species including *Lactococcus* sp., such as *L. lactis; Lactobacillus* sp., including *L. reuteri; Leuconostoc* sp.; *Pediococcus* sp.; and *Streptococcus* sp. Still other useful hosts include *Bacillus* sp. A 7-7, for example. Alternatively, strains of a Gram negative bacterial species belonging to Enterobacteriaceae, including *E. coli*, or to Pseudomonadaceae can be selected as the host organism.

A suitable yeast host organism can be selected from biotechnologically relevant yeasts species, such as, but not limited to, *Pichia* sp., *Hansenula* sp., *Kluyveromyces* sp., *Yarrowinia* sp., *Saccharomyces* sp., including *S. cerevisiae*, or a species belonging to *Schizosaccharomyces*, such as *S. pombe*. A strain of the methylotrophic yeast species *Pichia pastoris* can be used as the host organism. Alternatively, the host organism can be a *Hansenula* species. Suitable host organisms among filamentous fungi include species of *Aspergillus*, e.g., *A. niger, A. oryzae, A. tubigensis, A. awamori*, or *A. nidulans*. Alternatively, a strain of *Fusarium* sp., e.g., *Fusarium oxysporum* or *Rhizomucor* sp., such as *R. miehei*, can be used as the host organism. Other suitable yeasts include *Thermomyces* sp. and *Mucor* sp. Fungal cells may be transformed by a process involving protoplast formation and transformation of the protoplasts followed by regeneration of the cell wall in a manner known in the art. A suitable procedure for transforming *Aspergillus* host cells, for example, is described in EP 238023.

In a yet further aspect, a method of producing an α-amylase variant is provided, which method comprises cultivating a host cell as described above under conditions conducive to the production of the variant and recovering the variant from the cells and/or culture medium. The medium used to cultivate the cells may be any conventional medium suitable for growing the host cell in question and obtaining expression of the α-amylase variant. Suitable media and media components are available from commercial suppliers or may be prepared according to published recipes, e.g., as described in catalogues of the American Type Culture Collection (ATCC). Exemplary culture media include, but are not limited to, those for fed-batch fermentations performed in a three thousand liter (3,000 L) stirred tank fermentor. The media used would be that most suitable for the host cell being used, for example the media discussed below for culturing *Bacillus* sp. no. 707. The growth medium in that case can consist of corn steep solids and soy flour as sources of organic compounds, along with inorganic salts as a source of sodium, potassium, phosphate, magnesium and sulfate, as well as trace elements. Typically, a carbohydrate source such as glucose is also part of the initial medium. Once the culture has established itself and begins growing, the carbohydrate is metered into the tank to maintain the culture as is known in the art. Samples are removed from the fermentor at regular intervals to measure enzyme titer using, for example, a colorimetric assay method. The fermentation process is halted when the enzyme production rate stops increasing according to the measurements.

An α-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Host cells may be cultured under suitable conditions which allow expression of the α-amylase variant proteins. Expression of the proteins may be constitutive such that they are continually produced, or inducible, requiring a stimulus to initiate expression. In the case of inducible expression, protein production can be initiated when required by addition of an inducer substance, e.g., dexamethasone, IPTG, or Sepharose, to the culture medium, for example. Polypeptides can also be produced recombinantly in an in vitro cell-free system, such as the TnT™ (Promega) rabbit reticulocyte system.

An α-amylase variant expressing host also can be cultured under aerobic conditions in the appropriate medium for the host. Shaking or a combination of agitation and aeration can be provided, with production occurring at the appropriate temperature for that host, e.g., from about 30° C. to about 75° C., depending on the needs of the host and production of the desired α-amylase variant. Culturing can occur from about 12 to about 100 hours or greater (and any hour value there between) or more particularly from 24 to 72 hours. Typically, the culture broth is at a pH of about 5.5 to about 8.0, again depending on the culture conditions needed for the host cell relative to production of the α-amylase variant.

4. Purification of α-Amylase Variants

Fermentation, separation, and concentration techniques are known in the art and conventional methods can be used in order to prepare the concentrated α-amylase variant containing solution. After fermentation, a fermentation broth is obtained, and the microbial cells and various suspended solids, including residual raw fermentation materials, are removed by conventional separation techniques to obtain an amylase solution. Filtration, centrifugation, microfiltration, rotary vacuum drum filtration, followed by ultra-filtration, extraction or chromatography, or the like are generally used.

It is desirable to concentrate the solution containing the α-amylase variant to optimize recovery, since the use of unconcentrated solutions requires increased incubation time to collect precipitates containing the purified α-amylase variant. The solution is concentrated using conventional techniques until the desired enzyme level is obtained. Concentration of the enzyme variant containing solution may be achieved by any of the techniques discussed above. In one embodiment, rotary vacuum evaporation and/or ultrafiltration is used. Alternatively, ultrafiltration can be used.

By "precipitation agent" for purposes of purification is meant a compound effective to precipitate the α-amylase variant from the concentrated enzyme variant solution in solid form, whatever its nature may be, i.e., crystalline, amorphous, or a blend of both. Precipitation can be performed using, for example, a metal halide precipitation agent. Metal halide precipitation agents include: alkali metal chlorides, alkali metal bromides and blends of two or more of these metal halides. The metal halide may be selected from the group consisting of sodium chloride, potassium chloride, sodium bromide, potassium bromide and blends of two or more of these metal halides. Suitable metal halides include sodium chloride and potassium chloride, particularly sodium chloride, which can further be used as a preservative.

The metal halide precipitation agent is used in an amount effective to precipitate the α-amylase variant. The selection of at least an effective amount and an optimum amount of metal halide effective to cause precipitation of the enzyme variant, as well as the conditions of the precipitation for maximum recovery including incubation time, pH, temperature and concentration of α-amylase variant, will be readily apparent to one of ordinary skill in the art after routine testing.

Generally, at least about 5% w/v (weight/volume) to about 25% w/v of metal halide is added to the concentrated enzyme variant solution, and usually at least 8% w/v. Generally, no more than about 25% w/v of metal halide is added to the concentrated enzyme variant solution and usually no more than about 20% w/v. The optimal concentration of the metal halide precipitation agent will depend, among others, on the nature of the specific α-amylase variant and on its concentration in the concentrated α-amylase variant solution.

Another alternative to effect precipitation of the enzyme is to use of organic compounds, which can be added to the concentrated enzyme variant solution. The organic compound precipitating agent can include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously. For further descriptions, see, e.g., U.S. Pat. No. 5,281,526 to Genencor International, Inc, for example.

Generally, the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitations agents can be for example linear or branched alkyl esters of 4-hydroxybenzoic acid, wherein the alkyl group contains from 1 to 10 carbon atoms, and blends of two or more of these organic compounds. Suitable organic compounds include linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds can also be used. Additional organic compounds also include, but are not limited to, 4-hydroxybenzoic acid methyl ester (methyl PARABEN) and 4-hydroxybenzoic acid propyl ester (propyl PARABEN), which are also amylase preservative agents.

Addition of the said organic compound precipitation agent provides the advantage of high flexibility of the precipitation conditions with respect to pH, temperature, α-amylase variant concentration, precipitation agent concentration, and time of incubation.

The organic compound precipitation agent is used in an amount effective to improve precipitation of the enzyme variant by means of the metal halide precipitation agent. The selection of at least an effective amount and an optimum amount of organic compound precipitation agent, as well as the conditions of the precipitation for maximum recovery including incubation time, pH, temperature and concentration of enzyme variant, will be readily apparent to one of ordinary skill in the art, in light of the present disclosure, after routine testing.

Generally, at least 0.01% w/v of organic compound precipitation agent is added to the concentrated enzyme variant solution and usually at least 0.02% w/v. Generally, no more than 0.3% w/v of organic compound precipitation agent is added to the concentrated enzyme variant solution and usually no more than 0.2% w/v.

The concentrated enzyme variant solution, containing the metal halide precipitation agent and, in one aspect, the organic compound precipitation agent, is adjusted to a pH that necessarily will depend on the enzyme variant to be purified. Generally, the pH is adjusted to a level near the isoelectric point (pI) of the amylase. For example, the pH can be adjusted within a range of about 2.5 pH units below the pI to about 2.5 pH units above the pI. The pH may be adjusted accordingly if the pI of the variant differs from the wild-type pI.

The incubation time necessary to obtain a purified enzyme variant precipitate depends on the nature of the specific enzyme variant, the concentration of enzyme, and the specific precipitation agent(s) and its (their) concentration. Generally, the time effective to precipitate the enzyme variant is between about 1 to about 30 hours; usually it does not exceed about 25 hours. In the presence of the organic compound precipitation agent, the time of incubation can still be reduced to less than about 10 hours, and in most cases even about 6 hours.

Generally, the temperature during incubation is between about 4° C. and about 50° C. Usually, the method is carried out at a temperature between about 10° C. and about 45° C., and particularly between about 20° C. and about 40° C. The optimal temperature for inducing precipitation varies according to the solution conditions and the enzyme variant or precipitation agent(s) used.

The overall recovery of purified enzyme variant precipitate, and the efficiency with which the process is conducted, is improved by agitating the solution comprising the enzyme variant, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme variant is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration or the like. Cross membrane microfiltration can be one method used. Further purification of the purified enzyme variant precipitate can be obtained by washing the precipitate with water. For example, the purified enzyme variant precipitate is washed with water containing the metal halide precipitation agent, for example, with water containing the metal halide and the organic compound precipitation agents.

During the culturing, thermostable amylase extracellularly accumulates in the culture broth. For the isolation and purification of the desired α-amylase variant, the culture broth is centrifuged or filtered to eliminate cells, and the resulting cell-free liquid is used for the purification of the enzyme. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme variant active fraction. For further purification, a conventional procedure such as ion exchange chromatography may be used.

Purified enzyme variants are useful for all applications in which the enzyme variants are generally utilized. For example, they can be used in laundry detergents and spot removers, in the food industry, in starch processing and baking, and in pharmaceutical compositions as digestive aids. They can be made into a final product that is either liquid (solution, slurry) or solid (granular, powder).

Alternatively, the enzyme product can be recovered and a floccing agent is added to the media in order to remove cells and cell debris by filtration or centrifugation without further purification of the enzyme.

The α-amylase variants produced and purified by the methods described above can be used in a variety of useful industrial applications. The variants possess valuable properties facilitating applications related to fabric and household care (F&HC). For example, a variant can be used as a component in washing, dishwashing and hard-surface cleaning detergent compositions. Variants also are useful in the production of sweeteners and ethanol from starch, and/or for textile desizing. Variant α-amylases are particularly useful in starch-conversion processes, including starch liquefaction and/or saccharification processes, as described, for example, in WO 2005/111203 and U.S. Published Application No. 2006/0014265 (Genencor International, Inc.). These various uses of the α-amylase variants are described in more detail below.

5. Cleaning and Dishwashing Compositions and Use

The α-amylase variants discussed herein can be formulated in detergent compositions for use in cleaning dishes or other cleaning compositions, for example. These can be gels, powders or liquids. The compositions can comprise the α-amylase variant alone, other amylolytic enzymes, other cleaning enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

In the detergent applications, α-amylase variants are usually used in a liquid composition containing propylene glycol. The α-amylase variant can be solubilized in propylene glycol, for example, by circulating in a 25% volume/volume propylene glycol solution containing 10% calcium chloride.

The dishwashing detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxsulphonates.

Other suitable organic builders include the higher molecular weight polymers and co-polymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, optionally with a bleach precursor or as a peroxy acid compound. Typical examples of suitable peroxy bleach compounds are alkali metal perborates, both tetrahydrates and monohydrates, alkali metal percarbonates, persilicates, and perphosphates. Suitable activator materials include tetraacetylethylenediamine (TAED) and glycerol triacetate. Enzymatic bleach activation systems may also be present, such as perborate or percarbonate, glycerol triacetate and perhydrolase, as disclosed in WO 2005/056783, for example.

The cleaning composition may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester). The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescent agents, thickeners, and perfumes.

Finally, the α-amylase variants may be used in conventional dishwashing detergents, e.g., in any of the detergents described in the following patent publications, with the consideration that the α-amylase variants disclosed herein are used instead of, or in addition to, any α-amylase disclosed in the listed patents and published applications: CA 2006687, GB 2200132, GB 2234980, GB 2228945, DE 3741617, DE 3727911, DE 4212166, DE 4137470, DE 3833047, DE 4205071, WO 93/25651, WO 93/18129, WO 93/04153, WO 92/06157, WO 92/08777, WO 93/21299, WO 93/17089, WO 93/03129, EP 481547, EP 530870, EP 533239, EP 554943, EP 429124, EP 346137, EP 561452, EP 318204, EP 318279, EP 271155, EP 271156, EP 346136, EP 518719, EP 518720, EP 518721, EP 516553, EP 561446, EP 516554, EP 516555, EP 530635, EP 414197, and U.S. Pat. Nos. 5,112,518; 5,141, 664; and 5,240,632.

6. Laundry Detergent Compositions and Use

According to the embodiment, one or more α-amylase variants may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products; (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in U.S. Pat. No. 5,879,920 (Genencor International, Inc.) or EP 238216, for example. Polyols have long been recognized as stabilizers of proteins as well as for improving the solubility of proteins. See, e.g., Kaushik et al., "Why is trehalose an exceptional protein stabilizer? An analysis of the thermal stability of proteins in the presence of the compatible osmolyte trehalose" *J. Biol. Chem.* 278: 26458-65 (2003) and references cited therein; and M. Conti et al., "Capillary isoelectric focusing: the problem of protein solubility,"*J. Chromatography* 757: 237-245 (1997).

The detergent composition may be in any convenient form, e.g., as gels, powders, granules, pastes, or liquids. A liquid detergent may be aqueous, typically containing up to about 70% of water, and 0% to about 30% of organic solvent, it may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide, as described in WO 92/06154, for example.

The detergent composition may additionally comprise one or more other enzymes, such as lipase, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e., essentially free of detergent builder. Enzymes may be used in any composition compatible with the stability of the enzyme. Enzymes can be protected against generally deleterious components by known forms of encapsulation, as by granulation or sequestration in hydro gels, for example. Enzymes and specifically α-amylases either with or without the starch binding domains are not limited to laundry and dishwashing applications, but may bind use in surface cleaners and ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate optionally combined with a peracid-forming bleach activator, such as TAED or nonanoyloxybenzenesulfonate (NOBS). Alternatively, the bleaching system may comprise peroxy acids of the amide, imide, or sulfone type, for example. The bleaching system can also be an enzymatic bleaching system where a perhydrolase activates peroxide, such as that described in WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative, such as an aromatic borate ester; and the composition may be formulated as described in WO 92/19709 and WO 92/19708, for example.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, or perfume, for example. The pH (measured in aqueous solution at use concentration) is usually neutral or alkaline, e.g., pH about 7.0 to about 11.0.

The α-amylase variant may be incorporated in concentrations conventionally employed in detergents. It is at present contemplated that, in the detergent composition, the α-amylase variant may be added in an amount corresponding to 0.00001-1.0 mg (calculated as pure enzyme protein) of α-amylase variant per liter of wash liquor. Particular forms of detergent compositions comprising the α-amylase variants can be formulated to include:

(1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate, about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3.H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

(2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate, about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

(3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate, about 3% to about 9%; zeolite (as $NaAlSiO_4$) about 23% to about 33%; sodium sulfate (e.g., $Na_2SO_4$) 0% to about 4%; sodium perborate (e.g., $NaBO_3.H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

(4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate, about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

(5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

(6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers (e.g., lauryl methacrylate/acrylic acid copolymer); molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

(7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; soluble silicate, about 1% to about 4%; zeolite (e.g., $NaAlSiO_4$) about 20% to about 40%; sodium sulfate (e.g., $Na_2SO_4$) about 2% to about 8%; sodium perborate (e.g., $NaBO_3.H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

(8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate, about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

(9) A detergent composition formulated as a granulate comprising linear alkylbenzenesulfonate (calculated as acid)

about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3.H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

(10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

(11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer, such as lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

(12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates, about 5% to about 15%; sodium sulfate (e.g., $Na_2SO_4$) 0% to about 5%; zeolite ($NaAlSiO_4$) about 15% to about 28%; sodium perborate (e.g., $NaBO_3.H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

(13) Detergent compositions as described in compositions 1)-12) supra, wherein all or part of the linear alkylbenzenesulfonate is replaced by ($C_{12}$-$C_{18}$) alkyl sulfate.

(14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate, 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

(15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate, 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

(16) Detergent formulations as described in 1)-15) supra, which contain a stabilized or encapsulated peracid, either as an additional component or as a substitute for already specified bleach systems.

(17) Detergent compositions as described supra in 1), 3), 7), 9), and 12), wherein perborate is replaced by percarbonate.

(18) Detergent compositions as described supra in 1), 3), 7), 9), 12), 14), and 15), which additionally contains a manganese catalyst.

(19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

In another embodiment, the 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the detergent composition can comprise 2,6-β-D-fructan hydrolase, one or more α-amylase variants, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof. In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115. Suitable commercially available protease enzymes include Alcalase®, Savinase®, Esperase®, and Kannase™

(Novozymes, formerly Novo Nordisk A/S); Maxatase®, Maxacal™, Maxapem™, Properase™, Purafect®, Purafect OxP™, FN2™, and FN3™ (Genencor International, Inc.).

Lipases: suitable lipases include those of bacterial or fungal origin. Chemically modified or protein engineered mutants are included. Examples of useful lipases include, but are not limited to, lipases from *Humicola* (synonym *Thermomyces*), e.g. *H. lanuginosa* (*T. lanuginosus*) (see, e.g., EP 258068 and EP 305216) and *H. insolens* (see, e.g., WO 96/13580); a *Pseudomonas* lipase (e.g., from *P. alcaligenes* or *P. pseudoalcaligenes*; see, e.g., EP 218 272), *P. cepacia* (see, e.g., EP 331 376), *P. stutzeri* (see, e.g., GB 1,372,034), *P. fluorescens*, *Pseudomonas* sp. strain SD 705 (see, e.g., WO 95/06720 and WO 96/27002), *P. wisconsinensis* (see, e.g., WO 96/12012); a *Bacillus* lipase (e.g., from *B. subtilis*; see, e.g., Dartois et al. *Biochemica Biophysica Acta*, 1131: 253-360 (1993)), *B. stearothermophilus* (see, e.g., JP 64/744992), or *B. pumilus* (see, e.g., WO 91/16422). Additional lipase variants contemplated for use in the formulations include those described, for example, in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase® Ultra (Novozymes, formerly Novo Nordisk A/S).

Polyesterases: Suitable polyesterases include, but are not limited to, those described in WO 01/34899 (Genencor International, Inc.) and WO 01/14629 (Genencor International, Inc.), and can be included in any combination with other enzymes discussed herein.

Amylases: The compositions can be combined with other α-amylases, such as a non-variant α-amylase. These can include commercially available amylases, such as but not limited to Duramyl®, Termamyl™, Fungamyl® and BAN™ (Novozymes, formerly Novo Nordisk A/S), Rapidase®, and Purastar® (Genencor International, Inc.).

Cellulases: Cellulases can be added to the compositions. Suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, e.g., the fungal cellulases produced from *Humicola insolens*, *Myceliophthora thermophila* and *Fusarium oxysporum* disclosed in U.S. Pat. Nos. 4,435,307; 5,648,263; 5,691,178; 5,776,757; and WO 89/09259, for example. Exemplary cellulases contemplated for use are those having color care benefit for the textile. Examples of such cellulases are cellulases described in EP 0495257; EP 531 372; WO 99/25846 (Genencor International, Inc.), WO 96/34108 (Genencor International, Inc.), WO 96/11262; WO 96/29397; and WO 98/08940, for example. Other examples are cellulase variants, such as those described in WO 94/07998; WO 98/12307; WO 95/24471; PCT/DK98/00299; EP 531 315; U.S. Pat. Nos. 5,457,046; 5,686,593; and 5,763,254. Commercially available cellulases include Celluzyme® and Carezyme® (Novozymes, formerly Novo Nordisk A/S); Clazinase™ and Puradax® HA (Genencor International, Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive, i.e., a separate additive or a combined additive, can be formulated as a granulate, liquid, slurry, etc. Suitable granulate detergent additive formulations include non-dusting granulates.

Non-dusting granulates may be produced, e.g., as disclosed in U.S. Pat. Nos. 4,106,991 and 4,661,452 and optionally may be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591, for example. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition may be in any convenient form, e.g., a bar, tablet, gel, powder, granule, paste, or liquid. A liquid detergent may be aqueous, typically containing up to about 70% water, and 0% to about 30% organic solvent. Compact detergent gels containing 30% or less water are also contemplated. The detergent composition comprises one or more surfactants, which may be non-ionic, including semipolar, anionic, cationic, or zwitterionic, or any combination thereof. The surfactants are typically present at a level of from 0.1% to 60% by weight.

When included therein the detergent typically will contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose (CMC), poly(vinylpyrrolidone) (PVP), poly(ethylene glycol) (PEG), poly (vinyl alcohol) (PVA), poly(vinylpyridine-N-oxide), poly(vinylimidazole), polycarboxylates, e.g., polyacrylates, maleic/acrylic acid copolymers), and lauryl methacrylate/acrylic acid copolymers.

The detergent may contain a bleaching system that may comprise a source of $H_2O_2$, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g., the amide-, imide-, or sulfone-type peroxyacids). The bleaching system can also be an enzymatic bleaching system.

The enzyme(s) of the detergent composition may be stabilized using conventional stabilizing agents, e.g., polyol (e.g., propylene glycol or glycerol), a sugar or sugar alcohol, lactic acid, boric acid, a boric acid derivative (e.g., an aromatic borate ester), or a phenyl boronic acid derivative (e.g., 4-formylphenyl boronic acid). The composition may be formulated as described in WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is contemplated that in the detergent compositions, the enzyme variants may be added in an amount corresponding to about 0.01 to about 100 mg of enzyme protein per liter of wash liquor, particularly about 0.05 to about 5.0 mg of enzyme protein per liter of wash liquor, or even more particularly in 0.1 to about 1.0 mg of enzyme protein per liter of wash liquor.

6.1 Methods of Assessing Detergent Compositions

Numerous α-amylase cleaning assays exist. Exemplary description of testing cleaning includes the following. A "swatch" is a piece of material such as a fabric that has a stain applied thereto. The material can be, for example, fabrics made of cotton, polyester or mixtures of natural and synthetic fibers. Alternatively, the material can be paper, such as filter paper or nitrocellulose, or a piece of a hard material, such as ceramic, metal, or glass. For α-amylases, the stain is starch based, but can include blood, milk, ink, grass, tea, wine, spinach, gravy, chocolate egg, cheese, clay, pigment, oil, or mixtures of these compounds. In one embodiment, the α-amylase variant is tested in a BMI (blood/milk/ink) assay.

A "smaller swatch" is a piece of the swatch that has been cut with a single hole punch device, or a custom manufactured 96-hole punch device, where the pattern of the multi-hole punch is matched to standard 96-well microtiter plates, or has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch also can be made by applying a stain to a small piece of material. For example, the smaller swatch can be a piece of fabric with a stain ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived to deliver simultaneously swatches to any format plate, including, but not limited to, 24-well, 48-well, and 96-well plates. In another conceivable method, the soiled test platform can be a bead made of either metal, plastic, glass, ceramic, or other suitable material that is coated with the soil substrate. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis.

In one embodiment, a treatment protocol provides control over degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk--Testgewebe GmbH, Krefeld Germany; or Center for Test Materials, Vlaardingen, The Netherlands) and/or can be made by the practitioner (Morris and Prato, *Textile Research Journal* 52(4): 280-286 (1982)). Swatches can comprise, for example, a cotton-containing fabric containing a stain made by blood/milk/ink (BMI), spinach, grass, or chocolate/milk/soot. A BMI stain can be fixed to cotton with 0.0003% to 0.3% hydrogen peroxide, for example. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see, e.g., Cayot and Tainturier, *Anal. Biochem.* 249: 184-200 (1997)). However, if a detergent or an enzyme sample leads to the formation of unusually small peptide fragments (for example, from the presence of peptidases in the sample), then one will obtain a larger TNBS signal, i.e., more "noise."

Another means of measuring wash performance of blood/milk/ink that is based on ink release that can be quantified by measuring the absorbance of the wash liquor. The absorbance can be measured at any wavelength between 350 and 800 nm. In one embodiment, the wavelength is measured at 410 nm or 620 nm. The wash liquor can also be examined to determine the wash performance on stains containing grass, spinach, gelatin or Coomassie stain. Suitable wavelengths for these stains include and 670 nm for spinach or grass and 620 nm for gelatin or Coomassie. For example, an aliquot of the wash liquor (typically 100-150 μL from a 96-well microplate, for example) is removed and placed in a cuvette or multiwell microplate. This is then placed in a spectrophotometer and the absorbance is read at an appropriate wavelength. The system also can be used to determine a suitable enzyme and/or detergent composition for dish washing, for example, using a blood/milk/ink stain on a suitable substrate, such as cloth, plastic or ceramic.

In one aspect, a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate.

Into each well, a known mixture of a detergent composition and an enzyme such as a variant protein is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tests with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains.

7. Biofilm Removal Compositions and Use

The composition may comprise one variant α-amylase as the major enzymatic component, e.g., a mono-component composition for use in removing biofilms. Alternatively, the composition may comprise multiple enzymatic activities, such as multiple amylases, or a cocktail of enzymes including an aminopeptidase, amylase (β- or α- or gluco-amylase), carbohydrase, carboxypeptidase, catalase, cellulase, chitinase, cutinase, cyclodextrin glucanotranseferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, and/or xylanase, or any combination thereof for removing biofilms. The additional enzyme(s) may be producible by means of a microorganism belonging to the genus *Aspergillus*, e.g., *A. aculeatus, A. awamori, A. niger,* or *A. oryzae*; or *Trichoderma; Humicola*, e.g., *H. insolens*; or *Fusarium*, e.g., *F. bactridioides, F. cerealis, F. crookwellense, F. culmorum, F. graminearum, F. graminum, F. heterosporum, F. negundi, F. oxysporum, F. reticulatum, F. roseum, F. sambucinum, F. sarcochroum, F. sulphureum, F. toruloseum, F. trichothecioides,* or *F. venenatum*.

The α-amylase variant comprising compositions may be prepared in accordance with methods known in the art and may be in the form of a liquid or a dry composition. For instance, the α-amylase variant containing composition may be in the form of a granulate or a microgranulate. The polypeptide to be included in the composition may be stabilized in accordance with methods known in the art.

Examples are given below of uses of the polypeptide compositions. The dosage of the α-amylase variant containing composition and other conditions under which the composition is used may be determined on the basis of methods known in the art. The α-amylase variants are further contemplated for use in a composition along with a 2,6-β-D-fructan hydrolase or variant thereof.

One aspect is disintegration and/or removal of biofilm. The term "disintegration" as used herein is to be understood as hydrolysis of polysaccharides in a biofilm matrix connecting and binding together individual microbial cells in the biofilm, whereby the microbial cells can be released and removed from the biofilm. The biofilm may be present at a surface, and the disintegration of the biofilm can be achieved by bringing the surface in contact with an aqueous medium, e.g., by immersing, covering or splashing, where the aqueous medium comprises an α-amylase variant and optionally one or more enzymes responsible for breaking down biofilms, such as but not limited to 2,6-β-D-fructan hydrolase. The composition can be used to hydrolyse slime, e.g., in white waters in the pulping and paper industry.

The α-amylase variant may be present in the amount of 0.0001 to 10,000 mg/L, 0.001-1000 mg/L, 0.01-100 mg/L, or even 0.1-10 mg/L. Additional enzymes and enzyme variants may be present in similar amounts or less. The process may be performed at temperatures from about ambient temperature to about 70° C. A suitable temperature range is from about 30° C. to about 60° C., e.g., about 40° C. to about 50° C.

A suitable pH for the hydrolyzing biofilms lies within from about 3.5 to about 8.5. A particularly suitable pH range is from about 5.5 to about 8, e.g. from about 6.5 to about 7.5. The contact time or reaction time for the enzyme variant to effectively removing a biofilm may vary considerably, depending on the biofilm properties and the frequency of which a surface is treated with the enzyme variant alone or in combination with other enzymes, such as 2,6-β-D-fructan hydrolase, but a suitable reaction time lies within about 0.25 to about 25 hours. A particularly suitable reaction time is from about 1 to about 10 hours, e.g., about 2 hours.

Additional enzymes can be combined with the α-amylase variants and 2,6-β-D-fructan hydrolases, including, but not limited to, cellulases, hemicellulases, xylanases, other amylases including other α-amylases, lipases, proteases, and/or pectinases. The enzymes can further be combined with antimicrobial agents such as enzymatic or non-enzymatic biocides. An enzymatic biocide may be a composition comprising an oxidoreductase, e.g., a laccase or a peroxidase, especially haloperoxidase, and optionally an enhancing agent, such as an alkyl syringate, as described in WO 97/42825 and DK 97/1273, for example.

The surface from which a biofilm is to be removed and/or cleaned off may be a hard surface, which by definition relates to any surface which is essentially non-permeable to microorganisms. Examples are surfaces made from metal, e.g., stainless steel alloys, plastics/synthetic polymers, rubber, board, glass, wood, paper, textile, concrete, rock, marble, gypsum and ceramic materials which optionally may be coated with paint, enamel, polymers and the like. Accordingly, the surface may be a member of a system holding, transporting, processing, or contacting aqueous solutions, such as water supply systems, food processing systems, cooling systems, chemical processing systems, pharmaceutical processing systems, or wood processing system, such as found in the pulp and/or paper industry. Accordingly, the enzyme variants and compositions containing the enzyme variants are useful in a conventional cleaning-in-place (C-I-P) system. The surface may a member of a system unit such as pipes, tanks, pumps, membranes, filters, heat exchangers, centrifuges, evaporators, mixers, spray towers, valves and reactors. The surface may also be or be a part of utensils used in the medical science and industry such as contaminated endoscopes, prosthetic devices or medical implants.

The compositions for biofilm removal also are contemplated for preventing so-called bio-corrosion occurring when a metal surface, e.g., a pipeline, is attacked by a microbial biofilm. The compositions disintegrate the biofilm, thereby preventing the microbial cells of the biofilm from creating a biofilm environment that would corrode the metal surface to which it is attached.

7.1 Oral Care Compositions

Additional applications for anti-biofilm compositions include oral care. Surfaces thus include teeth with dental plaque. Accordingly, the variant enzymes can be used for compositions, e.g., toothpaste, and processes for making a medicament comprising an enzyme variant for disintegration of plaque present on a human or animal tooth. A further use is disintegration of biofilm from mucous membranes, such as biofilm in lungs in patients suffering from cystic fibrosis. The surface also may be other surfaces of biological origin, e.g., skin, teeth, hair, nails, or may be contaminated contact lenses.

Other enzymes useful in oral care compositions include, but are not limited to, 2,6-β-D-fructan hydrolase; dextranase; mutanases; oxidases, such as glucose oxidase; L-amino acid oxidase; peroxidases, such as *Coprinus* sp. peroxidases described in WO 95/10602 or lactoperoxidase; haloperoxidases, especially haloperoxidase from *Curvularia* sp., in particular *C. verruculosa* and *C. inaequalis*; laccases; proteases, such as papain; acidic protease (e.g., the acidic proteases described in WO 95/02044); endoglucosidases; lipases; amylases, including amyloglucosidases, such as AMG™ (Novozymes, formerly Novo Nordisk A/S); anti-microbial enzymes; and mixtures thereof.

The oral care composition may have any suitable physical form, i.e., powder, paste, gel, liquid, ointment, tablet, etc. An "oral care composition" includes a composition that can be used for maintaining or improving the oral hygiene in the mouth of humans and animals by preventing dental caries, preventing the formation of dental plaque and tartar, removing dental plaque and tartar, preventing and/or treating dental diseases, etc. Oral care compositions also encompass products for cleaning dentures, artificial teeth, and the like. Examples of oral care compositions include toothpaste, dental cream, gel or tooth powder, odontic mouthwashes, pre- or post brushing rinse formulations, chewing gum, lozenges, and candy. Toothpastes and tooth gels typically include abrasive polishing materials, foaming agents, flavoring agents, humectants, binders, thickeners, sweetening agents, whitening/bleaching/stain removing agents, water, and optionally enzymes. Mouthwashes, including plaque-removing liquids, typically comprise a water/alcohol solution, flavor, humectant, sweetener, foaming agent, colorant, and optionally enzymes.

Abrasive polishing material may also be incorporated into the oral care composition. Accordingly, abrasive polishing material can include alumina and hydrates thereof, such as α-alumina trihydrate; magnesium trisilicate; magnesium carbonate; kaolin; aluminosilicates, such as calcined aluminum silicate and aluminum silicate; calcium carbonate; zirconium silicate; and also powdered plastics, such as polyvinyl chloride; polyamides; polymethyl methacrylate; polystyrene; phenol-formaldehyde resins; melamine-formaldehyde resins; urea-formaldehyde resins; epoxy resins; powdered polyethylene; silica xerogels; hydrogels and aerogels and the like. Also suitable as abrasive agents are calcium pyrophosphate; water-insoluble alkali metaphosphates; dicalcium phosphate and/or its dihydrate, dicalcium orthophosphate; tricalcium phosphate; particulate hydroxyapatite and the like. It is also possible to employ mixtures of these substances. Depending on the oral care composition, the abrasive product may be present at about 0% to about 70% by weight, for example, from about 1% to about 70%. For toothpastes, the abrasive material content typically lies in the range of 10% to 70% by weight of the final toothpaste.

Humectants are employed to prevent loss of water from toothpastes, for example. Suitable humectants for use in oral care compositions include glycerol; polyol; sorbitol; polyethylene glycols (PEG); propylene glycol; 1,3-propanediol; 1,4-butanediol; hydrogenated partially hydrolyzed polysaccharides and the like and mixtures thereof. Humectants are in general present at 0% to about 80% or about 5% to about 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, are examples of suitable thickeners and binders that help stabilize a dentifrice product. Thickeners may be present in toothpaste creams and gels at about 0.1% to about 20% by weight, and binders at about 0.01 to about 10% by weight of the final product.

A foaming agent can be used, including soap, anionic, cationic, non-ionic, amphoteric and/or zwitterionic surfactants. These may be present at levels of 0% to about 15%, about 0.1 to about 13%, or even about 0.25% to about 10% by weight of the final product. Surfactants are only suitable to the extent that they do not inactivate the present enzymes. Surfactants include fatty alcohol sulfates, salts of sulphonated mono-glycerides or fatty acids having 10 to 20 carbon atoms, fatty acid-albumen condensation products, salts of fatty acids amides and taurines, and/or salts of fatty acid esters of isethionic acid.

Suitable sweeteners include saccharin for use in a formulation. Flavors, such as spearmint, also are usually present in low amounts, such as from about 0.01% to about 5% by weight, especially from about 0.1% to about 5%. Whitening/bleaching agents include $H_2O_2$ and may be added in amounts less than about 5% or from about 0.25% to about 4%, calculated by the weight of the final product. The whitening/bleaching agents may be an enzyme, such as an oxidoreductase. Examples of suitable teeth bleaching enzymes are described in WO 97/06775. Water is usually added in an amount giving the composition, e.g. toothpaste, a flowable form. Water-soluble anti-bacterial agents, such as chlorhexidine digluconate, hexetidine, alexidine, Triclosan®, quaternary ammonium anti-bacterial compounds and water-soluble sources of certain metal ions such as zinc, copper, silver and stannous (e.g., zinc, copper and stannous chloride, and silver nitrate) also may be included. Additional compounds that can be used include a fluoride source, dyes/colorants, preservatives, vitamins, pH-adjusting agents, anti-caries agents, desensitizing agents, etc.

Enzymes are also useful in the oral care compositions described above. Enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids which form the structural components of bacterial cell walls and membranes. Dextranase and other carbohydrases, such as the 2,6-β-D-fructan hydrolase, break down the organic skeletal structure produced by bacteria that forms a matrix for bacterial adhesion. Proteases and amylases not only prevent plaque formation, but also prevent the development of mineralization by breaking-up carbohydrate-protein complexes that bind calcium.

A toothpaste typically may comprise the following ingredients (in weight % of the final toothpaste composition): abrasive material to about 70%; humectant: 0% to about 80%; thickener: about 0.1% to about 20%; binder: about 0.01% to about 10%; sweetener: about 0.1% to about 5%; foaming agent: 0% to about 15%; whitener: 0% to about 5%; and enzymes: about 0.0001% to about 20%. In one embodiment, a toothpaste has a pH in the range from about 6.0 to about 8.0, and comprises: about 10% to about 70% abrasive material; 0% to about 80% humectant; 0.1% to about 20% thickener; 0.01% to about 10% binder; about 0.1% to about 5% sweetener; 0% to about 15% foaming agent; 0% to about 5% whitener; and about 0.0001% to about 20% enzymes. These enzymes include α-amylase variants alone or in combination with other enzymes, such as 2,6-β-D-fructan hydrolase, and optionally other types of enzymes mentioned above.

A mouthwash typically may comprise the following ingredients (in weight % of the final mouth wash composition): 0% to about 20% humectant; 0% to about 2% surfactant; 0% to about 5% enzymes; 0% to about 20% ethanol; 0% to about 2% other ingredients (e.g., flavor, sweetener active ingredients such as fluorides). The composition can also contain from about 0% to about 70% water. The mouthwash composition may be buffered with an appropriate buffer, e.g. sodium citrate or phosphate in the pH-range of about 6.0 to about 7.5. The mouthwash may be in none-diluted form, i.e., must be diluted before use. The oral care compositions may be produced using any conventional method known to the art of oral care.

8. Starch Processing Compositions and Use

In another aspect, compositions with the disclosed α-amylase variants can be utilized for starch liquefaction and/or saccharification. Starch processing is useful for producing sweetener, producing alcohol for fuel or drinking (i.e., potable alcohol), producing a beverage, processing cane sugar, or producing desired organic compounds, e.g., citric acid, itaconic acid, lactic acid, gluconic acid, ketones, amino acids, antibiotics, enzymes, vitamins, and hormones. Conversion of starch to fructose syrups normally consists of three consecutive enzymatic processes: a liquefaction process, a saccharification process, and an isomerization process. During the liquefaction process, a variant α-amylase degrades starch to dextrins by at pH between about 5.5 and about 6.2 and at temperatures of about 95° C. to about 160° C. for a period of approximately 2 hours. About 1 mM of calcium (40 ppm free calcium ions) typically is added to optimize enzyme stability under these conditions. Other α-amylase variants may require different conditions.

After the liquefaction process, the dextrins can be converted into dextrose by addition of a glucoamylase (e.g., AMG™) and optionally a debranching enzyme, such as an isoamylase or a pullulanase (e.g., Promozyme®). Before this step, the pH is reduced to a value below about 4.5, maintaining the high temperature (above 95° C.), and the liquefying α-amylase variant activity is denatured. The temperature is lowered to 60° C., and a glucoamylase and a debranching enzyme can be added. The saccharification process proceeds typically for about 24 to about 72 hours.

After the saccharification process, the pH is increased to a value in the range of about 6.0 to about 8.0, e.g., pH 7.5, and the calcium is removed by ion exchange. The dextrose syrup is then converted into high fructose syrup using an immobilized glucose isomerase (such as Sweetzyme®), for example.

The α-amylase variant may provide at least one improved enzymatic property for conducting the process of liquefaction. For example, the variant α-amylase may have a higher activity, or it may have a reduced requirement for calcium. Addition of free calcium is required to ensure adequately high stability of the α-amylase; however, free calcium strongly inhibits the activity of the glucose isomerase. Accordingly, the calcium should be removed prior to the isomerization step, by means of an expensive unit operation, to an extent that reduces the level of free calcium to below 3-5 ppm. Cost savings can be obtained if such an operation could be avoided, and the liquefaction process could be performed without addition of free calcium ions. Thus, α-amylase variants that do not require calcium ions or that have a reduced requirement for calcium are particularly advantageous. For example, a less calcium-dependent α-amylase variant, which is stable and highly active at low concentrations of free calcium (<40 ppm) can be utilized in the composition and procedures. Such an α-amylase variant should have a pH optimum in the range of about 4.5 to about 6.5, e.g., about pH 4.5 to about pH 5.5. The α-amylase variants can be used alone to provide specific hydrolysis or can be combined with other amylases to provide a "cocktail" with a broad spectrum of activity.

The starch to be processed may be a highly refined starch quality, for instance, at least 90%, at least 95%, at least 97%, or at least 99.5% pure. Alternatively, the starch can be a more crude starch containing material comprising milled whole grain, including non-starch fractions such as germ residues and fibers. The raw material, such as whole grain, is milled to open up the structure and allow further processing. Two milling processes are suitable: wet and dry milling. Also, corn grits, and milled corn grits may be applied. Dry milled grain will comprise significant amounts of non-starch carbohydrate compounds, in addition to starch. When such a heterogeneous material is processed by jet cooking, often only a partial gelatinization of the starch is achieved. Accordingly, α-amylase variants having a high activity towards ungelatinized starch are advantageously applied in a process comprising liquefaction and/or saccharification jet cooked dry milled starch.

A variant α-amylase having a superior hydrolysis activity during the liquefaction process advantageously increases the efficiency of the saccharification step (see WO 98/22613) and the need for glucoamylase during the saccharification step. The glucoamylase advantageously is present in an amount of no more than, or even less than, 0.5 glucoamylase activity unit (AGU)/g DS (i.e., glucoamylase activity units per gram of dry solids). The glucoamylase may be derived from a strain within *Aspergillus* sp., *Talaromyces* sp., *Pachykytospora* sp., or *Trametes* sp., with exemplary examples being *Aspergillus niger*, *Talaromyces emersonii*, *Trametes cingulata*, or *Pachykytospora papyracea*. In one embodiment, the process also comprises the use of a carbohydrate-binding domain of the type disclosed in WO 98/22613.

In yet another aspect, the process may comprise hydrolysis of a slurry of gelatinized or granular starch, in particular hydrolysis of granular starch into a soluble starch hydrolysate at a temperature below the initial gelatinization temperature of the granular starch. In addition to being contacted with an α-amylase variant, the starch may be contacted with one or more enzyme selected from the group consisting of a fungal α-amylase (EC 3.2.1.1), a β-amylase (EC 3.2.1.2), and a glucoamylase (EC 3.2.1.3). In an embodiment further another amylolytic enzyme or a debranching enzyme, such as an isoamylase (EC 3.2.1.68), or a pullulanases (EC 3.2.1.41) may be added to the α-amylase variant.

In one embodiment, the process is conducted at a temperature below the initial gelatinization temperature. Such processes are often conducted at least at 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or at least 60° C. The pH at which the process is conducted may in be in the range of about 3.0 to about 7.0, from about 3.5 to about 6.0, or from about 4.0 to about 5.0. One aspect contemplates a process comprising fermentation with a yeast, for example, to produce ethanol at a temperature around 32° C., such as from 30° C. to 35° C. In another aspect, the process comprises simultaneous saccharification and fermentation with a yeast to produce ethanol or with another suitable fermentation organism to produce a desired organic compound, for example, at a temperature from 30° C. to 35° C., e.g., at around 32° C. In the above fermentation processes, the ethanol content reaches at least about 7%, at least about 8%, at least about 9%, at least about 10%, at least about 11%, at least about 12%, at least about 13%, at least about 14%, at least about 15%, or at least about 16% ethanol.

The starch slurry to be used in any of the above aspects may have about 20% to about 55% dry solids granular starch, about 25% to about 40% dry solids granular starch, or about 30% to about 35% dry solids granular starch. The enzyme variant converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, the α-amylase variant is used in a process for liquefaction or saccharification of a gelatinized starch, including, but not limited to, gelatinization by jet cooking. The process may comprise fermentation to produce a fermentation product, e.g., ethanol. Such a process for producing ethanol from starch-containing material by fermentation comprises: (i) liquefying the starch-containing material with an α-amylase variant; (ii) saccharifying the liquefied mash obtained; and (iii) fermenting the material obtained in step (ii) in the presence of a fermenting organism. Optionally the process further comprises recovery of the ethanol. The saccharification and fermentation processes may be carried out as a simultaneous saccharification and fermentation (SSF) process. During the fermentation, the ethanol content reaches at least about 7%, at least about 8%, at least about 9%, at least about 10% such as at least about 11%, at least about 12%, at least about 13%, at least about 14%, at least 15%, or at least 16% ethanol.

The starch to be processed in the above aspects may be obtained from tubers, roots, stems, legumes, cereals or whole grain. More specifically, the granular starch may be obtained from corns, cobs, wheat, barley, rye, milo, sago, cassava, tapioca, sorghum, rice, peas, bean, banana, or potatoes. Specially contemplated are both waxy and non-waxy types of corn and barley.

As used herein, the term "liquefaction" or "liquefy" means a process by which starch is converted to less viscous and shorter chain dextrins. Generally, this process involves gelatinization of starch simultaneously with or followed by the addition of an α-amylase variant. Additional liquefaction-inducing enzymes optionally may be added. As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from about 90-150° C., e.g., 100-110° C. Subsequent to application to a heat exchange or jet temperature, the slurry is held for a period of 3-10 minutes at that temperature. This step of holding the slurry at 90-150° C. is termed primary liquefaction.

As used herein, the term "secondary liquefaction" refers the liquefaction step subsequent to primary liquefaction (heating to 90-150° C.), when the slurry is allowed to cool to room temperature. This cooling step can be 30 minutes to 180 minutes, e.g. 90 minutes to 120 minutes. As used herein, the term "minutes of secondary liquefaction" refers to the time that has elapsed from the start of secondary liquefaction to the time that the Dextrose Equivalent (DE) is measured.

Another aspect contemplates the additional use of a β-amylase in the composition comprising the α-amylase variant. β-amylases (EC 3.2.1.2) are exo-acting maltogenic amylases, which catalyze the hydrolysis of 1,4-α-glucosidic linkages into amylose, amylopectin, and related glucose polymers, thereby releasing maltose. β-amylases have been isolated from various plants and microorganisms (Fogarty et al., PROGRESS IN INDUSTRIAL MICROBIOLOGY, Vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Genencor International, Inc.); and Novozym™ WBA (Novozymes A/S).

Another enzyme contemplated for use in the composition is a glucoamylase (EC 3.2.1.3). Glucoamylases are derived from a microorganism or a plant. For example, glucoamylases can be of fungal or bacterial origin. Exemplary bacterial glucoamylases are Aspergillus glucoamylases, in particular A. niger G1 or G2 glucoamylase (Boel et al. (1984), EMBO J. 3(5): 1097-1102), or variants thereof, such as disclosed in WO 92/00381 and WO 00/04136; A. awamori glucoamylase (WO 84/02921); A. oryzae glucoamylase (Agric. Biol. Chem. (1991), 55(4): 941-949), or variants or fragments thereof.

Other contemplated Aspergillus glucoamylase variants include variants to enhance the thermal stability: G137A and G139A (Chen et al. (1996), Prot. Eng. 9: 499-505); D257E and D293E/Q (Chen et al. (1995), Prot. Eng. 8: 575-582); N182 (Chen et al. (1994), Biochem. J 301: 275-281); disulphide bonds, A246C (Fierobe et al. (1996), Biochemistry, 35: 8698-8704); and introduction of Pro residues in positions A435 and S436 (Li et al. (1997) Protein Eng. 10: 1199-1204). Other contemplated glucoamylases include Talaromyces glucoamylases, in particular derived from T. emersonii (WO 99/28448), T. leycettanus (U.S. Pat. No. RE 32,153), T. duponti, or T. thermophilus (U.S. Pat. No. 4,587,215). Contemplated bacterial glucoamylases include glucoamylases from the genus Clostridium, in particular C. thermoamylolyticum (EP 135138) and C. thermohydrosulfuricum (WO 86/01831). Suitable glucoamylases include the glucoamylases derived from Aspergillus oryzae, such as a glucoamylase having 50%, 55%, 60%, 65%, 70%, 75%, 80%, 85%, or even 90% homology to the amino acid sequence shown in SEQ ID NO:2 in WO 00/04136. Also suitable are commercial glucoamylases, such as AMG 200L; AMG 300 L; SAN™ SUPER and AMG™ E (Novozymes); OPTIDEX® 300 (Genencor International, Inc.); AMIGASE™ and AMIGASE™ PLUS (from DSM); G-ZYME® G900 (Enzyme Bio-Systems); and G-ZYME® G990 ZR (A. niger glucoamylase and low protease content). Glucoamylases may be added in an amount of 0.02-2.0 AGU/g DS or 0.1-1.0 AGU/g DS, e.g., 0.2 AGU/g DS.

Additional enzyme variants can be included in the composition. Two or more α-amylase variants can be used alone or in combination with other enzymes discussed herein. For example, a third enzyme may be another α-amylase, e.g., a yeast α-amylase, or another α-amylase variant. These can be Bacillus α-amylases or non-Bacillus α-amylases.

Another enzyme that can optionally be added is a debranching enzyme, such as an isoamylase (EC 3.2.1.68) or a pullulanases (EC 3.2.1.41). Isoamylase hydrolyses α-1,6-D-glucosidic branch linkages in amylopectin and n-limit dextrins and can be distinguished from pullulanases by the inability of isoamylase to attack pullulan and by the limited action of isoamylase on α-limit dextrins. Debranching enzymes may be added in effective amounts well known to the person skilled in the art.

The exact composition of the products of the process depends on the combination of enzymes applied, as well as the type of granular starch processed. The soluble hydrolysate may be maltose with a purity of at least about 85%, at least about 90%, at least about 95.0%, at least about 95.5%, at least about 96.0%, at least about 96.5%, at least about 97.0%, at least about 97.5%, at least about 98.0%, at least about 98.5%, at least about 99.0% or at least about 99.5%. Alternatively, the soluble starch hydrolysate is glucose, or the starch hydrolysate has a DE (glucose percent of total solubilized dry solids) of at least 94.5%, at least 95.0%, at least 95.5%, at least 96.0%, at least 96.5%, at least 97.0%, at least 97.5%, at least 98.0%, at least 98.5%, at least 99.0% or at least 99.5%. In one embodiment, a process of manufacturing ice creams, cakes, candies, canned fruit uses a specialty syrup containing a mixture of glucose, maltose, DP3 and DPn.

Two milling processes are suitable: wet milling and dry milling. In dry milling, the whole kernel is milled and used. Wet milling gives a good separation of germ and meal (starch granules and protein) and is usually used when the starch hydrolysate is used in production of syrups. Both dry and wet milling are well known in the art of starch processing and also are contemplated for use with the compositions and methods disclosed. The process may be conducted in an ultrafiltration system where the retentate is held under recirculation in presence of enzymes, raw starch and water, where the permeate is the soluble starch hydrolysate. Another method is the process conducted in a continuous membrane reactor with ultrafiltration membranes, where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate.

In one regard, the soluble starch hydrolysate of the process is subjected to conversion into high fructose starch-based syrup (HFSS), such as high fructose corn syrup (HFCS). This conversion can be achieved using a glucose isomerase, particularly a glucose isomerase immobilized on a solid support. Contemplated isomerases included the commercial products Sweetzyme®, IT (Novozymes A/S); G-zyme® IMGI, and G-zyme® G993, Ketomax®, G-zyme® G993, G-zyme® G993 liquid, and GenSweet® IGI.

In another aspect, the soluble starch hydrolysate of produced yields production of fuel or potable ethanol. In the process of the third aspect the fermentation may be carried out simultaneously or separately/sequential to the hydrolysis of the granular starch slurry. When the fermentation is performed simultaneously with the hydrolysis, the temperature can be between 30° C. and 35° C., particularly between 31° C. and 34° C. The process may be conducted in an ultrafiltration system where the retentate is held under recirculation in presence of enzymes, raw starch, yeast, yeast nutrients and water and where the permeate is an ethanol containing liquid. Also contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta-lactone, or sodium erythorbate.

The amylolytic activity of the α-amylase variant may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

9. Textile Desizing Compositions and Use

Also contemplated are compositions and methods of treating fabrics (e.g., to desize a textile) using one or more of the α-amylase variants. The α-amylase variants can be used in any fabric-treating method, which are well known in the art (see, e.g., U.S. Pat. No. 6,077,316). For example, in one aspect, the feel and appearance of a fabric is improved by a method comprising contacting the fabric with an enzyme variant in a solution. In one aspect, the fabric is treated with the solution under pressure.

In one aspect, the enzymes are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The α-amylase variant can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme variant. The α-amylase variant can be used alone or with other desizing chemical reagents and/or desizing enzymes to desize fabrics, including cotton-containing fabrics, as detergent additives, e.g., in aqueous compositions. The α-amylase variant can also be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. The α-amylase variant can be used in methods of finishing denim garments (e.g., a "bio-stoning process"), enzymatic desizing and providing softness to fabrics, and/or finishing process.

10. Compositions and Methods for Baking and Food Preparation

For the commercial and home use of flour for baking and food production, it is important to maintain an appropriate level of α-amylase activity in the flour. A level of activity that is too high may result in a product that is sticky and/or doughy and unmarketable; but flour with insufficient α-amylase activity may not contain enough sugar for proper yeast function, resulting in dry, crumbly bread. Accordingly, an α-amylase variant polypeptide, by itself or in combination with another α-amylase(s), may be added to the flour to augment the level of endogenous α-amylase activity in flour. The α-amylase typically has a temperature optimum in the presence of starch in the ranges of 30-90° C., 50-80° C., 55-75° C., or 60-70° C., for example. The temperature optimum may be measured in a 1% solution of soluble starch at pH 5.5.

In addition to the use of grains and other plant products in baking, grains such as barley, oats, wheat, as well as plant components, such as corn, hops, and rice are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. An α-amylase variant polypeptide, by itself or in combination with another α-amylase(s), accordingly may be added to the components used for brewing.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

An α-amylase variant polypeptide further can be added alone or in a combination with other amylases to prevent or retard staling, i.e., crumb firming of baked products. The amount of anti-staling amylase will typically be in the range of 0.01-10 mg of enzyme protein per kg of flour, e.g., 1-10 mg/kg. Additional anti-staling amylases that can be used in combination with an α-amylase variant polypeptide include an endo-amylase, e.g., a bacterial endo-amylase from *Bacillus*. The additional amylase can be a maltogenic α-amylase (EC 3.2.1.133), e.g., from *Bacillus*. Novamyl® is a suitable maltogenic α-amylase from *B. stearothermophilus* strain NCIB 11837 and is described in Christophersen et al., *Starch*, 50(1): 39-45 (1997). Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soy bean, or from microbial sources, such as *Bacillus*.

The baking composition comprising an α-amylase variant polypeptide further can comprise a phospholipase. The phospholipase may have $A_1$ or $A_2$ activity to remove fatty acid from the phospholipids, forming a lyso-phospholipid. It may or may not have lipase activity, i.e., activity on triglycerides. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, such as the genus or species *Aspergillus, A. niger; Dictyostelium, D. discoideum; Mucor, M. javanicus, M. mucedo, M. subtilissimus; Neurospora, N. crassa; Rhizomucor, R. pusillus; Rhizopus, R. arrhizus, R. japonicus, R. stolonifer; Sclerotinia, S. libertiana; Trichophyton, T. rubrum; Whetzelinia, W. sclerotiorum; Bacillus, B. megaterium, B. subtilis; Citrobacter, C. freundii; Enterobacter, E. aerogenes, E. cloacae; Edwardsiella, E. tarda; Etwinia, E. herbicola; Escherichia, E. coli; Klebsiella, K. pneumoniae; Proteus, P. vulgaris; Providencia, P. stuartii; Salmonella, S. typhimurium; Serratia, S. liquefasciens, S. marcescens; Shigella, S. flexneri; Streptomyces, S. violeceoruber; Yersinia, Y. enterocolitica; Fusarium, F. oxysporum*, strain DSM 2672), for example.

A phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 Lipase Unit (LU)/kg of flour, where a Lipase Unit is defined as the amount of enzyme required to release 1 μmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, *sorghum* meal, *sorghum* flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (either whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a hemicellulase, in particular a pentosanase such as xylanase, a protease, a protein disulfide isomerase, e.g., a protein disulfide isomerase as disclosed in WO 95/00636, for example, a glucanotranseferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipoxygenase, an L-amino acid oxidase or a carbohydrate oxidase. The additional enzyme may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*, in particular of *A. aculeatus, A. niger* (e.g., WO 91/19782), *A. awamori* (e.g., WO 91/18977), or *A. tubigensis* (e.g., WO 92/01793); from a strain of *Trichoderma*, e.g., *T. reesei*, or from a strain of *Humicola*, e.g., *H. insolens* (e.g., WO 92/17573). Pentopan® and Novozym 384® are commercially available xylanase preparations produced from *Trichoderma reesei*. The amyloglucosidase may be an *A. niger* amyloglucosidase (such as AMG®). Other useful amylase products include Grindamyl® A 1000 or A 5000 (available from Grindsted Products, Denmark). The glucose oxidase may be a fungal glucose oxidase, in particular an *Aspergillus niger* glucose oxidase (such as Gluzyme®). An exemplary protease is Neutrase®. An exemplary lipase can be derived from strains of *Thermomyces (Humicola), Rhizomucor, Candida, Aspergillus, Rhizopus*, or *Pseudomonas*, in particular from *Thermomyces lanuginosus (Humicola lanuginosa), Rhizomucor miehei, Candida antarctica, Aspergillus niger, Rhizopus delemar* or *Rhizopus arrhizus* or *Pseudomonas cepacia*. In specific embodiments, the lipase may be Lipase A or Lipase B derived from *Candida antarctica* as described in WO 88/02775, for example, or the lipase may be derived from *Rhizomucor miehei* as described in EP 238,023, for example, or *Humicola lanuginosa*, described in EP 305,216, for example, or *Pseudomonas cepacia* as described in EP 214,761 and WO 89/01032, for example.

The process may be used for any kind of baked product prepared from dough, either of a soft or a crisp character, either of a white, light or dark type. Examples are bread, particularly white, whole-meal or rye bread, typically in the form of loaves or rolls, French baguette-type bread, pita bread, tortillas, cakes, pancakes, biscuits, cookies, pie crusts, crisp bread, steamed bread, pizza and the like.

In another embodiment, an α-amylase variant polypeptide may be used in a pre-mix, comprising flour together with an anti-staling amylase, a phospholipase and a phospholipid. The pre-mix may contain other dough-improving and/or bread-improving additives, e.g., any of the additives, including enzymes, mentioned above. In one aspect, the α-amylase variant polypeptide is a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 μm. Granulates and agglomerated powders may be prepared by conventional methods, e.g., by spraying the α-amylase variant polypeptide onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Another aspect contemplates the enveloping of particles comprising an α-amylase variant polypeptide, i.e., α-amylase particles. To prepare the enveloped α-amylase particles, the enzyme is contacted with a food grade lipid in sufficient quantity so as to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils which are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary in order to provide the baker with some insurance against inadvertent under-measurement errors by the baker. The lower limit of enzyme concentration is determined by the minimum anti-staling effect the baker wishes to achieve.

A method of preparing a baked good may comprise: (a) preparing lipid-coated α-amylase particles, wherein substantially 100 percent of the α-amylase particles are coated; (b) mixing a dough containing flour; (c) adding the lipid-coated α-amylase to the dough before the mixing is complete and terminating the mixing before the lipid coating is removed from the α-amylase; (d) proofing the dough; and (e) baking the dough to provide the baked good, wherein the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results generally can be achieved when 25% of the oil specified in a bread dough formula is held out of the dough and is used as a carrier for a concentrated enveloped α-amylase when added near the end of the mix cycle. In bread or other baked goods, recipes which have extremely low fat content (such as French-style breads), it has been found that an enveloped α-amylase mixture of approximately 1% of the dry flour weight is sufficient to admix the enveloped α-amylase properly with the dough, but the range of percentages that may work is extremely wide and depends on the formula, finished product, and production methodology requirements of the individual baker. Second, the enveloped α-amylase suspension should be added to the mix with enough time remaining in the mix cycle for complete mixture into the dough, but not so early that excessive mechanical action will strip the protective lipid coating from a large proportion of the enveloped α-amylase particles.

In another embodiment, bacterial α-amylase (BAA) is added to the lipid-coated particles comprising an α-amylase variant polypeptide. BAA reduces bread to a gummy mass due to its excessive thermostability and retained activity in the fully baked loaf of bread; however, when BAA is incorporated into the lipid-coated particles, substantial additional anti-staling protection is obtained, even at very low BAA dosage levels. For example, BAA dosages of 150 RAU (Reference Amylase Units) per 100 pounds of flour have been found to be effective. In one embodiment, between about 50 to 2000 RAU of BAA is added to the lipid-coated enzyme product. This low BAA dosage level, combined with the ability of the protective coating to keep enzyme in the fully-baked loaf from free contact with the starches (except when water vapor randomly releases the enzyme from its coating), helps to achieve very high levels of anti-staling activity without the negative side-effects of BAA.

It will be apparent to those skilled in the art that various modifications and variation can be made to the compositions and methods of using same without departing from the spirit or scope of the intended use. Thus, it is the modifications and variations provided they come within the scope of the appended claims and their equivalents.

All references cited above are herein incorporated by reference in their entirety for all purposes.

EXAMPLES

Example 1

As an initial step in the development of an α-amylase variant, an α-amylase was chosen that exhibited advantageous performance characteristics in the various formulations described above. A representative α-amylase is from *Bacillus* sp. no. 707 (SEQ ID NO:1, residues 34-518 of Swissprot Accession No. P19571).

Next, an α-amylase was identified that exhibits superior expression in a host cell and that has relatively close sequence identity to the *Bacillus* sp. no. 707 α-amylase. Such an α-amylase is the *Bacillus* sp. A 7-7 (DSM 12368) α-amylase (SEQ ID NO:2; see also GenBank Accession No. CAL48155, SEQ ID NO:7).

A comparison of the mature amino acid sequences of these α-amylases is shown in FIG. 1 and below, where the top sequence is from *Bacillus* sp. no. 707 α-amylase (SEQ ID NO: 1) and the bottom sequence is from *Bacillus* sp. A 7-7 (DSM 12368) α-amylase (SEQ ID NO: 2). Only 33 amino acid positions differ in the 485 amino acid sequence, providing a sequence identity in the mature proteins of about 93%. The amino acid positions that differ in the two sequences are highlighted below.

```
1           11          21          31          41          51
HHNGTNGTMM  QYFEWYLPND  GNHWNRLNSD  ASNLKSKGIT  AVWIPPAWKG
ASQNDVGYGA
HHNGTNGTMM  QYFEWYLPND  GNHWNRLRSD  ASNLRDKGIT  AVWIPPAWKG
ASQNDVGYGA 61          71          81          91          101         111
YDLYDLGEFN  QKGTVRTKYG  TRSQLQAAVT  SLRNGIQVY   GDVVMNHKGG
ADATEMVRAV
YDLYDLGEFN  QKGTVRTKYG  TRNQLQAAVT  NLRSNGIQVY  GDVVMNHKGG
ADATEWVRAV
```

-continued

```
121         131         141         151         161         171
EVNF N NRNQE VF C E YTIEAW TR FDFPGRGN TH S S FKWRWY HFDGVDWDQS
FR LN NRIYKF
EVNF S NRNQE VS C D YTIEAW TK FDFPGRGN TH S N FKWRWY HFDGVDWDQS
FQ LQ NRIYKF 181         191         201         211         221         231
RC H GK N WDWE VDTENGNYDY LMYADIDMDH PEVVNELRNW GVWYTNTLGL
DGFRIDAVKH
RC D GK S WDWE VDTENGNYDY LMYADIDMDH PEVVNELRNW GVWYTNTLGL
DGFRIDAVKH 241         251         261         271         281         291
IKYSFTRDW I N HVR S A TGKN MFAVAEFWKN D I GAIENYL S KTNWNHSVFD
VPLHYNLYNA
IKYSFTRDW I T HVR N T TGKN MFAVAEFWKN D L GAIENYL N KTNWNHSVFD
VPLHYNLYNA 301         311         321         331         341         351
S R SGGNYDMR N IFNGTVVQR HF S HAVTFVD NHDSQPEEAL ESFVEEWFKP
LAYALTLTR E
S K SGGNYDMR Q IFNGTVVQR HF T HAVTFVD NHDSQPEEAL ESFVEEWFKP
LAYALTLTR D 361         371         381         391         401         411
QGYPSVFYGD YYGIPTHGVP AM R SKIDPIL EARQKYAYGK QNDYLDHHN I
IGWTREGNTA QGYPSVFYGD YYGIPTHGVP AM K SKIDPIL EARQKYAYGK
QNDYLDHHN M IGWTREGNTA 421         431         441         451         461         471
HPNSGLATIM SDC N GC S KWM F VGRNKAGQV W S DITGNF T G TVTINADGWG
NFSVNGGSVS HPNSGLATIM SDC D GC N KWM Y VGRNKAGQV W R DITGNF S G
TVTINADGWG NFSVNGGSVS

481
IWVI K Bacillus sp. no. 707 α-amylase (SEQ ID NO: 1)
IWVI N Bacillus sp. A 7-7 (DSM 12368) α-amylase (SEQ ID NO: 2)
```

Example 2

Amino acids that differ in the two sequences are then evaluated for the potential effect on expression of the substitution of the amino acid found in the *Bacillus* sp. no. 707 α-amylase with the amino acid found in *Bacillus* sp. A 7-7 (DSM 12368) α-amylase. In this case, a 3D structural model was created for each proposed variant, where the 3D structural model was based on known α-amylase crystal structures. The 3D structural model for *Bacillus* sp. no. 707 α-amylase has a Protein Database Brookhaven PDB/RSCB Protein Data Bank Accession Number of 1WPC. The structural model was used to evaluate the exposure of a particular amino acid to solvent and the extent to which a given substitution would destabilize the protein structure. Finally, the structural model was used to predict the effect of a particular substitution on the hydrophobicity of the enzyme surface for the variant. It is expected that substitutions of amino acids that are exposed to the solvent and that decrease the hydrophobicity of the protein will improve the expression of the variant. Table 1 below lists the various possible amino acid changes and assesses each in light of these criteria.

TABLE 1

| Amino acid substitution | Location in Domain/Secondary Structure | Expected relative beneficial effect of substitution | Further description |
| --- | --- | --- | --- |
| N28R | A/α-helix | ++ | totally solvent exposed, R might be less polar |
| S36D | A/α-helix | ++ | solvent exposed, D will increase solubility |
| S83N | A/α-helix | + | fully solvent exposed, S->N is a minor change |
| S91A | A/α-helix | − | close to 28, A might make the situation worse |
| N94S | A/α-helix | − | again same area, S is not a big change |
| M116W | B/β-sheet | ++ | very exposed, M is anyway problematic (prone to oxidation) |
| N125S | B | − | small change, no effect on solubility |
| T132S | B | − | minor change, a bit closer to active site |
| E134D | B | − | fully solvent exposed, no big effect expected |
| R142K | B/β-sheet | + | might reduce hydrophobicity, K is a minor change |
| S154N | B | − | small change, minor effect |
| R172Q | B | ++ | prominent solvent exposed |
| N174Q | B | − | even closer, but very minor change |
| H183D | B | ++ | very solvent exposed on top of a little extension |
| A186G | B | + | this minor change reduces hydrophobicity, but might be de-stabilizing |
| I250L | A/α-helix | − | buried residue, stability rather than solubility |
| N251T | A/α-helix | + | solvent exposed, but small change |
| S255N | A/α-helix | ++ | extremely solvent exposed, slight reduction of hydrophobicity |
| A256T | A/α-helix | ++ | extremely solvent exposed, improvement of solubility |

TABLE 1-continued

| Amino acid substitution | Location in Domain/Secondary Structure | Expected relative beneficial effect of substitution | Further description |
|---|---|---|---|
| L272I | A/α-helix | − | hydrophobic-hydrophobic exchange, no effect |
| Q280S | A/α-helix | − | partially buried, expect no big change |
| K302R | A/α-helix | − | fully solvent exposed, R is more hydrophobic than K |
| N311Q | A/α-helix | − | solvent exposed, but minor change |
| S323T | A | − | close to C domain, solvent exposed, small change |
| E360D | A | − | interface C-domain, solvent exposed, minor change |
| R383K | A/α-helix | − | close to C-domain, fully solvent exposed, minor change |
| I410M | C/β-sheet | − | hydrophobic area, partially buried, M = negative change in stability |
| A434P | C | − | hydrophobicity will be increased, might be stabilising |
| S437N | C/β-sheet | − | solvent exposed, small change, no effect expected |
| F441Y | C/β-sheet | + | solvent exposed, slight improvement of solubility |
| S452R | C/β-sheet | + | fully solvent exposed, R is not the best, K, N or D might be better |
| T459S | C | − | solvent exposed, small change |
| K485N | C | + | big change, not fully solvent exposed |

Example 3

Based on the structural modeling disclosed above, the following substitutions are expected to be particularly advantageous: N28R, S36D, M116W, R172Q, H183D, S255N and A256T. Also expected to be advantageous are the substitutions S83N, R142K, A186G, N251T, F441Y, S452R and K485N. Substitutions can be made by protein engineering techniques well known in the art, as described, for example, in Sambrook et al., MOLECULAR CLONING: A LABORATORY MANUAL, 2$^{nd}$ ed., Cold Spring Harbor, 1989 and 3$^{rd}$ ed., 2001. Variants are expressed and purified by the techniques described above, for example. Variants are further evaluated by specific activity and by the level of variant protein recovered from the fermentation broth, compared to the wild-type protein.

Variants may contain single amino acid substitutions or combinations of substitutions, including substitutions of all of the 14 residues disclosed above or subsets thereof. Subsets of mutations can be made and tested using combinatorial libraries of mutants. For example, a nucleotide encoding the protein having all 14 mutations may be digested into fragments with a restriction endonuclease, where each restriction fragment encodes one or more mutation. A library can be constructed by randomly mixing various mutated and wild-type gene fragments and ligating them together, using ligation procedures well known in the art. The resulting nucleic acids are selected that encode the full length protein with various subsets of mutations.

Example 4

Construction of 707 Amylase Mutants for Improved Expression

Six Amy707 amylase mutants (N28R, S36D, R172Q, H183D, S255N and A256T) and one double mutation (S36D/S255N) were constructed to improve their expression.

A codon optimized, synthetic *Bacillus* sp. no.707 amylase gene was ordered from GeneArt Inc. (Toronto, Canada) and cloned as a XhoI fragment (PCR with primers EBS2XhoI_RV and PlatXho5_FW) into vector pICatH (FIG. 20 in patent WO/2005/052146). The orientation of the Amy707 gene with respect to the CAT gene was determined by PCR and one clone in which both genes had the same orientation (ori1) was selected and designated pICatH-Amy707(ori1) (FIG. 3).

```
EBS2XhoI_RV:
                                         (SEQ ID NO: 9)
5'TGG AAT CTC GAG GTT TTA TCC TTT ACC TTG TCT
CC 3'

Plat5XhoI_FW:
                                        (SEQ ID NO: 10)
5' CCC CCG CTC GAG GCT TTT CTT TTG GAA GAA AAT
ATA GGG AAA ATG GTA CTT GTT AAA AAT TCG AAA TAT
TTA TAC AAT ATC ATA TGT TTC ACA TTG AAA GGG G 3'
``` pICatH-Amy707(ori1) was transformed into a competent *B. subtilis* strain (BG3594comK). The *B. subtilis* strain was made competent by induction of the comK gene under the control of a xylose inducible promoter (Hahn et al., Mol. Microbiol., 21:763-775 [1996]).

pICatH-Amy707(ori) plasmid DNA was isolated form *B. subtilis* cells using Qiagen miniprep kit. Dam methylation of plasmid pICatH-Amy707 amylase was performed using 50 uL miniprep DNA (~10-20 ng/uL), 10 uL dam methylase 10× buffer (NEB), 0.2 uL of S-adenosyl methionine, 4 uL of dam methylase, 36 uL of sterile water at 37° C. for 4 hours. The reaction product was isolated using QiaQuik (Qiagen columns) and the plasmid DNA eluted in 30 uL buffer EB (Qiagen).

The methylated pICatH-707 amylase plasmid was subjected to Quick-Change Multi-Site mutagenesis (QCMS) using the QuikChange® XL Multi Site-Directed Mutagenesis kit from Stratagene, La Jolla, Calif. The reaction mixture was prepared following manufacturer's recommendations, and consisted of: 15 µL sterile water, 2.5 µL reaction buffer, 1 µL dNTP mix, 0.5 µL Quik solution, 0.5 µL forward primer (25 uM), 0.5 µL reverse primer (25 uM), 4 µL pICatH-707 amylase methylated and purified plasmid (~20-30 ng total), 1 µL PfuTurbo® DNA polymerase, for a total of 25 uL. Cycling conditions: 95° C. 1 min 1X; 95° C. 1 min 1X, 55° C. 1 min 1X, 65° C. 18 min 30X (X denoted number of cycles).

```
The primers used were as follows:
                                        (SEQ ID NO: 11)
707N28R-F 5'ACCATT GGA ACC GCC TGC GCA GCG AT 3'

(SEQ ID NO: 12)
707N28R-R 5'CAG GTT GCT CGC ATC GCT GCG CAG GC 3'

(SEQ ID NO: 13)
707S36D-F 5'GAT GCG AGC AAC CTG AAA GAT AAA GG 3'
```

```
                                                          (SEQ ID NO: 14)
707S36D-R 5'ACT GCT GTG ATG CCT TTA TCT TTC AGG

TT3'

(SEQ ID NO: 15)
707R172Q-F 5'GAT TGG GAT CAA AGC CGC CAG CTG AAC

A3'

(SEQ ID NO: 16)
707R172Q-R 5'AGA TGC GGT TGT TCA GCT GGC GGC TTT3'

(SEQ ID NO: 17)
707H183D-F 5'ATC TAT AAA TTT CGC GGC GAT GGC AAA3'

(SEQ ID NO: 18)
707H183D-R 5'CAA TCC CAT GCT TTG CCA TCG CCG CGA3'

(SEQ ID NO: 19)
707S255N-F 5'TGG ATC AAT CAT GTC AGA AAC GCG

ACG3'

(SEQ ID NO: 20)
707S255N-R 5'CAT ATT TTT GCC CGT CGC GTT TCT

GAC3'

(SEQ ID NO: 21)
707A256T-F 5'CAA TCA TGT CAG AAG CAC GAC GGG

CAA A3'

(SEQ ID NO: 22)
707A256T-R 5'CAT ATT TTT GCC CGT CGT GCT TCT

GAC3'
```

Following QCMS PCR, 1 uL of restriction enzyme DpnI was added to the QCMS reaction and incubated at 37° C. for 4 hours. An additional 0.5 uL of DpnI was added and the reactions incubated at 37° C. for an additional 2 hours. 1 uL DpnI-digested QCMS reaction in 5 uL of sample buffer was incubated at 95° C. for 3 min, cooled to 4° C. and amplified using rolling circle amplification (RCA) TempliPhi kit (Amersham Cat #256400). 5 uL of reaction buffer and 0.2 uL of Phi29 polymerase were added to the DpnI-digested QCMS reaction and incubated for 30° C. for 16 hrs. After completion of reaction, the enzyme was inactivated as per Amersham's protocol.

The rolling circle amplication reactions were diluted 10 fold in deionized water and 2 ul of DNA was used to transform 100 uL of Bacillus subtilis (genotype: ΔaprE, ΔnprE, Δepr, ΔispA, Δbpr, degU$^{Hy}$32, oppA, ΔspoIIE3501, amyE::xylRPxylAcomK-ermC) competent cells and induced with xylose. The transformation reactions were plated onto LB Agar+10 ppm neomycin+1% insoluble starch plates and grown at 37° C. overnight.

Four colonies for each mutagenesis reaction were selected and individually resuspended in 20 uL of sterile water in microtiter plates and used for colony PCR using puReTaq Ready-To-Go PCR Beads (GE Healthcare). The reaction consisted of 2 uL of cell suspension, 22 uL of water, and 0.5 uL each of 707 PCR F1 & R1 primers (each as 25 uM stock, sequences listed below) and PureTaq beads.

```
                                                          (SEQ ID NO: 23)
707 PCR F1: 5' GCA AGT TCA CCA TGC AGT GTG TGA

C 3'

(SEQ ID NO: 24)
707 PCR R1: 5' TAT CAA GCT TAT CGA TAC CGT CGA

C 3'
```

Cycling conditions were: 95° C. 4 min 1x; 95° C. 1 min, 53° C. 1 min., 72° C. 1 min, 25x: 72° C. 5 min 1x. An agarose gel was run to confirm that the Colony PCR reaction had been successful. ExoSAP-IT (GE Healthcare) was used to remove primers and dNTPS. 5 uL of PCR product was added to 2 uL of ExoSAP-IT reagent and the reaction incubated at 37° C. for 15 min followed by 80° C. for 15 min.

Clones were sent to Sequetech Corporation (Mountain View, Calif.) for sequencing analysis using the following primers:

```
                                                          (SEQ ID NO: 25)
707 seq F1: 5' CGA TTG TGA GGA GTG GCT TGT G 3'

(SEQ ID NO: 26)
707 seq R1: 5' CTT ATC GAT ACC GTC GAC CCT C 3'
```

Clones (N28R-1, S36D-4, R172Q-4, H183D-1, S255N-7, or A256T-2) were streaked on LB plates supplemented with 5 ug/mL chloramphenicol and 1% insoluble starch and grown at 37° C. overnight. The plasmids were isolated using standard techniques.

The host B. licheniformis (Δmpr, Δapr, Δcat) was transformed with a plasmid vector from one of the previously sequenced clones using a protoplast method in a manner known per se. Transformants were obtained for the Amy707 amylase, N28R, S36D, R172Q, H183D, and S255N. All transformant strains had the gene of interest (either Amy707 or a variant) integrated into the host genome and the plasmid DNA looped out.

Example 5

Protein Expression in Shake Flasks

The transformed B. licheniformis cells were amplified to 75 ug/mL chloramphenicol (CMP) by using shake flasks in a stepwise manner from 5 ug/mL CMP to 75 ug/mL CMP and then plated until single, starch clearing colonies were obtained. Transformants obtained for R172Q, H183D and S36D/S255N in B. licheniformis cells were integrated, looped out, and amplified to grow at 50 ug/mL CMP. Transformants obtained for N28R, S36D, and S255N in B. licheniformis were integrated and looped-out and grown at 5 ug/mL CMP.

For growth in shake flasks, single colonies of variants were picked, inoculated in a tall glass tube containing 5 mL LB+chloramphenicol at appropriate concentration, and grown for 5-6 hours to yield a preculture. 250 mL baffled shake flasks were filled with 50 mL shake flask culture media (potassium phosphate based, 4% lactose, 2% Nutrisoy) and inoculated with 1 mL preculture and incubated at 37° C. at 250 rpm for 90 hours. Aliquots were subjected to centrifugation to collect culture supernatant, which was assayed for amylase activity or frozen at −20° C. until further use.

Example 6

In this example, the amylase activity of Bacillus sp. no. 707 amylase and 707 amylase single position variants (R172Q, H183D, and S255N) and two-position variant (S36D/S255N) expressed in *B. licheniformis* and grown in shake flasks was tested using Megazyme Ceralpha Assay as described below.

Megazyme Ceralpha Assay for Amylase activity

Figure 4:
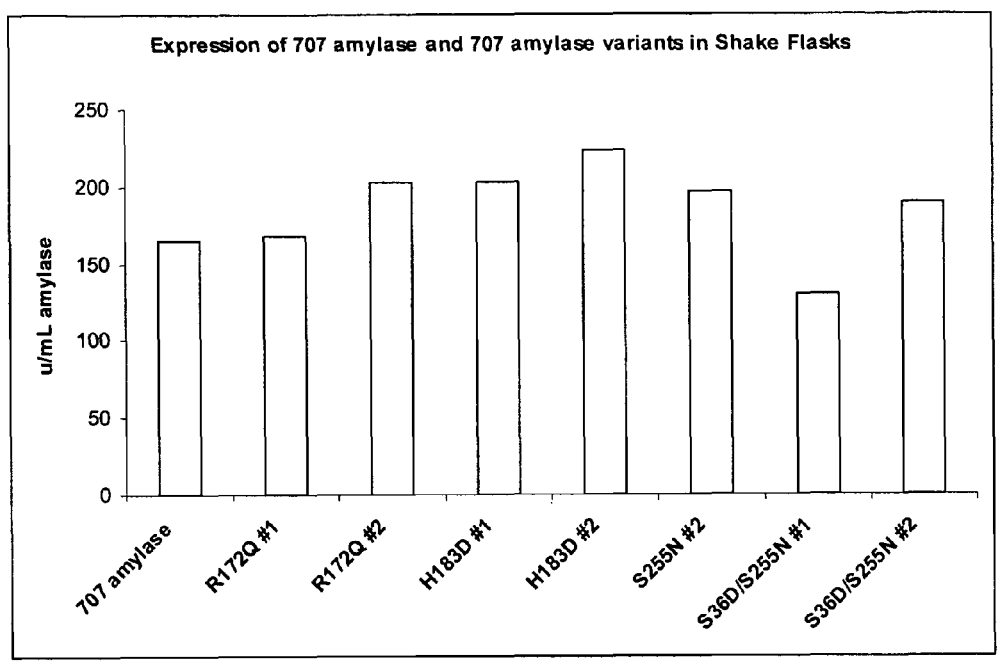
FIG. 4 depicts a comparison of amylase activity for a series of amylase 707 variants (R172Q, H183D, and S255N) in comparison to the parent enzyme.

This assay is a modification of the published protocols for Megazyme endo alpha-amylase Kit K-CERA 08/05 (AOAC Method 2002.01, Megazyme International Ireland). Reagent vials contain the substrate, which is non-reducing end-blocked p-nitrophenyl maltoheptaoside (BPNPG7, 54.5 mg) and thermostable alpha glucosidase (125 U at pH 6.0). To perform the assay, entire contents of one vial are dissolved in 10.0 mL of distilled water. 2 mL aliquots were stored frozen in 15 ml screw cap tubes. 6 mL assay buffer (50 mM Na malate, 2.6 mM $CaCl_2$, 50 mM NaCl, 0.002% Triton X-100, pH 6.7) was added to each tube prior to use. 0.79 mL substrate solution in buffer was added to a (preferably masked) cuvette. The cuvette was placed in the holder and a blank reading was obtained. Ten μL enzyme samples (diluted in assay buffer) were then added to the cuvette and the assay started. Absorbance per minute was measured at 400 nm or 410 nm and the values corrected for dilution and protein concentration. The amylase activity for each variant is reported in arbitrary units and shown in FIG. 4.

All references cited above are herein incorporated by reference in their entirety for all purposes.

---

What is claimed is:

1. A recombinant variant α-amylase, having α-amylase activity, having at least 97% amino acid sequence identity to SEQ ID NO: 1, and comprising a substitution corresponding to $H^{183}D$, using SEQ ID NO: 1 for numbering.

* * * * *

SEQUENCE LISTING

<160> NUMBER OF SEQ ID NOS: 27

<210> SEQ ID NO 1
<211> LENGTH: 485
<212> TYPE: PRT
<213> ORGANISM: Bacillus sp.

<400> SEQUENCE: 1

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270
```

```
Gly Ala Ile Glu Asn Tyr Leu Gln Lys Thr Asn Trp Asn His Ser Val
            275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
                435                 440                 445

Gln Val Trp Ser Asp Ile Thr Gly Asn Arg Thr Gly Thr Val Thr Ile
                450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160
```

```
His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 3
<211> LENGTH: 516
<212> TYPE: PRT
<213> ORGANISM: Bacillus sp.

<400> SEQUENCE: 3

Met Arg Lys Arg Lys Asn Gly Leu Ile Ser Ile Leu Leu Ala Phe Leu
1               5                   10                  15

Leu Val Leu Thr Ser Ile Pro Phe Thr Ser Ala Asn Val Glu Ala His
            20                  25                  30

His Asn Gly Thr Asn Gly Thr Met Met Gln Tyr Phe Glu Trp Tyr Leu
        35                  40                  45
```

```
Pro Asn Asp Gly Asn His Trp Asn Arg Leu Arg Ser Asp Ala Ser Asn
 50                  55                  60

Leu Lys Asp Lys Gly Ile Thr Ala Val Trp Ile Pro Pro Ala Trp Lys
 65                  70                  75                  80

Gly Ala Ser Gln Asn Asp Val Gly Tyr Gly Ala Tyr Asp Leu Tyr Asp
                 85                  90                  95

Leu Gly Glu Phe Asn Gln Lys Gly Thr Val Arg Thr Lys Tyr Gly Thr
                100                 105                 110

Arg Asn Gln Leu Gln Ala Ala Val Thr Ala Leu Lys Ser Asn Gly Ile
                115                 120                 125

Gln Val Tyr Gly Asp Val Val Met Asn His Lys Gly Ala Asp Ala
130                 135                 140

Thr Glu Trp Val Arg Ala Val Glu Val Asn Pro Ser Asn Arg Asn Gln
145                 150                 155                 160

Glu Val Ser Gly Asp Tyr Thr Ile Glu Ala Trp Thr Lys Phe Asp Phe
                165                 170                 175

Pro Gly Arg Gly Asn Thr His Ser Asn Phe Lys Trp Arg Trp Tyr His
                180                 185                 190

Phe Asp Gly Val Asp Trp Asp Gln Ser Arg Gln Leu Gln Asn Arg Ile
                195                 200                 205

Tyr Lys Phe Arg Gly Asp Gly Lys Gly Trp Asp Trp Glu Val Asp Thr
210                 215                 220

Glu Asn Gly Asn Tyr Asp Tyr Leu Met Tyr Ala Asp Ile Asp Met Asp
225                 230                 235                 240

His Pro Glu Val Val Asn Glu Leu Arg Asn Trp Gly Val Trp Tyr Thr
                245                 250                 255

Asn Thr Leu Gly Leu Asp Gly Phe Arg Ile Asp Ala Val Lys His Ile
                260                 265                 270

Lys Tyr Ser Phe Thr Arg Asp Trp Leu Thr His Val Arg Asn Thr Thr
                275                 280                 285

Gly Lys Asn Met Phe Ala Val Ala Glu Phe Trp Lys Asn Asp Ile Gly
                290                 295                 300

Ala Ile Glu Asn Tyr Leu Ser Lys Thr Asn Trp Asn His Ser Val Phe
305                 310                 315                 320

Asp Val Pro Leu His Tyr Asn Leu Tyr Asn Ala Ser Arg Ser Gly Gly
                325                 330                 335

Asn Tyr Asp Met Arg Gln Ile Phe Asn Gly Thr Val Val Gln Arg His
                340                 345                 350

Pro Thr His Ala Val Thr Phe Val Asp Asn His Asp Ser Gln Pro Glu
                355                 360                 365

Glu Ala Leu Glu Ser Phe Val Glu Glu Trp Phe Lys Pro Leu Ala Tyr
370                 375                 380

Ala Leu Thr Leu Thr Arg Asp Gln Gly Tyr Pro Ser Val Phe Tyr Gly
385                 390                 395                 400

Asp Tyr Tyr Gly Ile Pro Thr His Gly Val Pro Ala Met Lys Ser Lys
                405                 410                 415

Ile Asp Pro Ile Leu Glu Ala Arg Gln Lys Tyr Ala Tyr Gly Lys Gln
                420                 425                 430

Asn Asp Tyr Leu Asp His His Asn Met Ile Gly Trp Thr Arg Glu Gly
                435                 440                 445

Asn Thr Ala His Pro Asn Ser Gly Leu Ala Thr Ile Met Ser Asp Gly
                450                 455                 460

Pro Gly Gly Asn Lys Trp Met Tyr Val Gly Arg Asn Lys Ala Gly Gln
465                 470                 475                 480
```

Val Trp Arg Asp Ile Thr Gly Asn Arg Ser Gly Thr Val Thr Ile Asn
            485                 490                 495

Ala Asp Gly Trp Gly Asn Phe Ser Val Asn Gly Gly Ser Val Ser Ile
            500                 505                 510

Trp Val Asn Asn
        515

<210> SEQ ID NO 4
<211> LENGTH: 1554
<212> TYPE: DNA
<213> ORGANISM: Bacillus sp.

<400> SEQUENCE: 4

| | | | | | |
|---|---|---|---|---|---|
| atgaaaatga | gaacaggaaa | aaagggtttt | ttaagtattt | tattagcgtt | cttattggtg | 60 |
| attacttcaa | taccgtttac | tttagtagat | gtagaagcac | atcataacgg | tacgaacggg | 120 |
| acaatgatgc | aatactttga | atggtatcta | cctaatgacg | gaaatcattg | gaatcgatta | 180 |
| aactctgatg | cgagtaaacct | aaaagcaaa | gggattacag | cggtgtggat | tcctccagca | 240 |
| tggaagggcg | cttctcaaaa | tgacgtagga | tacggagcct | atgacctgta | tgatctggga | 300 |
| gaatttaatc | aaaaaggtac | cgtccgtaca | aaatatggaa | cacgtagtca | gttacaagct | 360 |
| gcggtaaccct | ccttaaaaaa | taatggaatt | caagtatatg | gtgacgttgt | tatgaatcac | 420 |
| aaaggtggcg | cagacgctac | tgaaatggta | agggccgttg | aagtgaatcc | caataaccgt | 480 |
| aaccaagaag | tgactggtga | atataccatt | gaagcttgga | ctagatttga | ttttccaggg | 540 |
| cgaggaaata | ctcattctag | ctttaaatgg | agatggtatc | attttgatgg | tgtggattgg | 600 |
| gatcagtcac | gtagactgaa | caatcgcatc | tataaattta | gaggtcatgg | caaagcttgg | 660 |
| gattgggaag | ttgatacgga | aaatggtaat | tatgattatt | taatgtacgc | tgatattgat | 720 |
| atggatcacc | cagaagtagt | aaatgaatta | agaaattggg | gtgtttggta | cacaaacaca | 780 |
| ttaggactcg | atggatttag | aatagatgcg | gttaaacata | taaagtatag | ctttacgcgc | 840 |
| gattggatta | tcacgttag | aagtgcaaca | ggtaaaaata | tgtttgcggt | tgctgagttt | 900 |
| tggaagaatg | atttaggtgc | aattgaaaac | tatctgcaga | aaacaaactg | gaaccattca | 960 |
| gtctttgatg | tgccgttaca | ttataatctt | tataatgcat | caaaaagcgg | agggaactat | 1020 |
| gatatgcgaa | acatatttaa | tggaacggtt | gttcaacgac | atccaagtca | tgctgtaaca | 1080 |
| tttgttgata | tcatgattc | gcagcctgaa | gaagcattag | aatcttttgt | tgaagaatgg | 1140 |
| tttaaaccat | tagcgtatgc | gcttacatta | acgcgtgaac | aaggatacccc | ttctgtattt | 1200 |
| tacggagatt | attatgggat | tccaacacat | ggagtgccag | caatgagatc | aaaaatcgat | 1260 |
| ccgatttag | aagcacgtca | aaagtatgca | tacgaaaaac | aaaatgatta | cttagaccat | 1320 |
| cataatatca | ttggttggac | gcgtgaaggg | aatacagcac | accccaattc | aggtctagct | 1380 |
| accatcatgt | ctgatggagc | gggtggaagt | aagtggatgt | tgttgggcg | taataaggct | 1440 |
| ggtcaagtat | ggagtgatat | tacaggaaac | cgtacaggta | cggttacaat | caatgcagac | 1500 |
| ggttggggca | atttctctgt | gaatggaggg | tcagtttcta | tttgggtcaa | caaa | 1554 |

<210> SEQ ID NO 5
<211> LENGTH: 1452
<212> TYPE: DNA
<213> ORGANISM: Bacillus sp.

<400> SEQUENCE: 5
caccataatg gcacaaatgg aacaatgatg caatattttg aatggtattt gccaaatgac    60

-continued

```
ggtaatcatt ggaatagatt aagatcagat gcaagtaatc ttaaagataa agggattaca       120
gcggtttgga taccacctgc ttggaaaggg gcttctcaaa atgatgtagg gtatggagcc       180
tatgatctgt atgatttagg agaattcaat caaaaaggaa ccgtacgtac aaagtacgga       240
acccgtaatc aattacaagc tgcagtaacc gccttaaaaa gtaatggtat tcaagtatac       300
ggagatgtcg taatgaatca taagggtgga gcggatgcca ctgagtgggt tcgagcggtt       360
gaagtgaacc caagtaatcg taatcaagaa gtctctggtg attatacgat tgaggcttgg       420
actaagtttg attttcctgg tcgaggtaat acccactcta actttaaatg gagatggtat       480
catttcgatg gtgtagattg ggatcagtca cgtcaattgc agaatcgaat ctataaattc       540
agaggagatg gaaaaggttg ggactgggaa gttgatacag agaacggaaa ctatgactat       600
ctaatgtacg cggatattga tatggatcac cctgaagtag tgaatgaact cagaaactgg       660
ggtgtatggt ataccaatac actggggcta gacgggttca gaatagatgc ggtaaaacat       720
ataaaatata gctttactcg tgattggctt actcacgtta gaaatacgac aggtaaaaat       780
atgtttgcag ttgcagagtt ctggaagaat gacataggtg caattgaaaa ttacttaagt       840
aaaacaaatt ggaatcattc agttttttgat gtgcccctgc attataaacct ttataatgca       900 tcgagaagtg gtggcaatta tgatatgagg caaatattta atggaacagt tgttcagaga       960
catcctacac atgctgtaac attttgttgat aaccatgatt cacagccgga agaagcccta      1020
gagtcatttg ttgaagagtg gttcaaaccg ttagcgtatg ctctcacact aacacgtgat      1080
caaggatatc cttccgtttt ttatggagat tattatggga ttccgacgca tggtgtacca      1140
gcaatgaaat ctaagattga tccgatttta gaagcacgtc aaaagtatgc gtacggaaaa      1200
caaaatgatt atttggatca ccataaatatg attggctgga cgcgtgaagg taatacagca      1260
catcccaact caggactagc aactattatg tcggatggcc caggaggaaa taaatggatg      1320
tatgttgggc gtaataaggc tggacaagtt tggagagata ttacaggaaa tcgctcaggt      1380
acggtgacga ttaacgcaga tgggtgggt aattttttctg taaatggtgg gtctgtatct      1440
atatgggtaa at                                                           1452
```

<210> SEQ ID NO 6
<211> LENGTH: 1551
<212> TYPE: DNA
<213> ORGANISM: Bacillus sp.

<400> SEQUENCE: 6

```
atgacgatga gaaaacgtaa aaatggatta atcagtattc tattggcatt tttgttggta        60
cttacatcaa tacctttta ttcagcaaac gtagaagcac accataatgg cacaaatgga       120
acaatgatgc aatattttga atggtatttg ccaaatgacg gtaatcattg aatagatta       180 agatcagatg caagtaatct taaagataaa gggattacag cggtttggat accacctgct       240
tggaaagggg cttctcaaaa tgatgtaggg tatggagcct atgatctgta tgatttagga       300
gaattcaatc aaaaaggaac cgtacgtaca aagtacggaa cccgtaatca attacaagct       360
gcagtaaccg ccttaaaaag taatggtatt caagtatacg gagatgtcgt aatgaatcat       420
aagggtggag cggatgccac tgagtgggtt cgagcggttg aagtgaaccc aagtaatcgt       480
aatcaagaag tctctggtga ttatacgatt gaggcttgga ctaagtttga ttttcctggt       540
cgaggtaata cccactctaa ctttaaatgg agatggtatc atttcgatgg tgtagattgg       600
gatcagtcac gtcaattgca gaatcgaatc tataaattca gaggagatgg aaaaggttgg       660
gactgggaag ttgatacaga gaacggaaac tatgactatc taatgtacgc ggatattgat       720
```

```
atggatcacc ctgaagtagt gaatgaactc agaaactggg gtgtatggta taccaataca    780
ctggggctag acgggttcag aatagatgcg gtaaaacata taaaatatag ctttactcgt    840
gattggctta ctcacgttag aaatacgaca ggtaaaaata tgtttgcagt tgcagagttc    900
tggaagaatg catagtggc aattgaaaat tacttaagta aaacaaattg gaatcattca    960
gtttttgatg tgcccctgca ttataacctt tataatgcat cgagaagtgg tggcaattat   1020
gatatgaggc aaatatttaa tggaacagtt gttcagagac atcctacaca tgctgtaaca   1080
tttgttgata accatgattc acagccggaa gaagccctag agtcatttgt tgaagagtgg   1140
ttcaaaccgt tagcgtatgc tctcacacta acacgtgatc aaggatatcc ttccgttttt   1200
tatggagatt attatgggat tccgacgcat ggtgtaccag caatgaaatc taagattgat   1260
ccgattttag aagcacgtca aaagtatgcg tacggaaaac aaaatgatta tttggatcac   1320
cataatatga ttggctggac gcgtgaaggt aatacagcac atcccaactc aggactagca   1380
actattatgt cggatggccc aggaggaaat aaatggatgt atgttgggcg taataaggct   1440
ggacaagttt ggagagatat tacaggaaat cgctcaggta cggtgacgat taacgcagat   1500
gggtggggta attttctgt aaatggtggg tctgtatcta tatgggtaaa t             1551
```

<210> SEQ ID NO 7
<211> LENGTH: 484
<212> TYPE: PRT
<213> ORGANISM: Bacillus sp.

<400> SEQUENCE: 7

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240
```

```
Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn

<210> SEQ ID NO 8
<211> LENGTH: 517
<212> TYPE: PRT
<213> ORGANISM: Bacillus sp.

<400> SEQUENCE: 8

Met Thr Met Arg Lys Arg Lys Asn Gly Leu Ile Ser Ile Leu Leu Ala
1               5                   10                  15

Phe Leu Leu Val Leu Thr Ser Ile Pro Phe Thr Ser Ala Asn Val Glu
            20                  25                  30

Ala His His Asn Gly Thr Asn Gly Thr Met Met Gln Tyr Phe Glu Trp
        35                  40                  45

Tyr Leu Pro Asn Asp Gly Asn His Trp Asn Arg Leu Arg Ser Asp Ala
    50                  55                  60

Ser Asn Leu Lys Asp Lys Gly Ile Thr Ala Val Trp Ile Pro Pro Ala
65                  70                  75                  80

Trp Lys Gly Ala Ser Gln Asn Asp Val Gly Tyr Gly Ala Tyr Asp Leu
                85                  90                  95

Tyr Asp Leu Gly Glu Phe Asn Gln Lys Gly Thr Val Arg Thr Lys Tyr
            100                 105                 110

Gly Thr Arg Asn Gln Leu Gln Ala Ala Val Thr Ala Leu Lys Ser Asn
        115                 120                 125
```

Gly Ile Gln Val Tyr Gly Asp Val Met Asn His Lys Gly Gly Ala
130             135             140

Asp Ala Thr Glu Trp Val Arg Ala Val Glu Val Asn Pro Ser Asn Arg
145                 150                 155                 160

Asn Gln Glu Val Ser Gly Asp Tyr Thr Ile Glu Ala Trp Thr Lys Phe
                165                 170                 175

Asp Phe Pro Gly Arg Gly Asn Thr His Ser Asn Phe Lys Trp Arg Trp
                180                 185                 190

Tyr His Phe Asp Gly Val Asp Trp Asp Gln Ser Arg Gln Leu Gln Asn
        195                 200                 205

Arg Ile Tyr Lys Phe Arg Gly Asp Gly Lys Gly Trp Asp Trp Glu Val
210                 215                 220

Asp Thr Glu Asn Gly Asn Tyr Asp Tyr Leu Met Tyr Ala Asp Ile Asp
225                 230                 235                 240

Met Asp His Pro Glu Val Val Asn Glu Leu Arg Asn Trp Gly Val Trp
                245                 250                 255

Tyr Thr Asn Thr Leu Gly Leu Asp Gly Phe Arg Ile Asp Ala Val Lys
                260                 265                 270

His Ile Lys Tyr Ser Phe Thr Arg Asp Trp Leu Thr His Val Arg Asn
        275                 280                 285

Thr Thr Gly Lys Asn Met Phe Ala Val Ala Glu Phe Trp Lys Asn Asp
290                 295                 300

Ile Gly Ala Ile Glu Asn Tyr Leu Ser Lys Thr Asn Trp Asn His Ser
305                 310                 315                 320

Val Phe Asp Val Pro Leu His Tyr Asn Leu Tyr Asn Ala Ser Arg Ser
                325                 330                 335

Gly Gly Asn Tyr Asp Met Arg Gln Ile Phe Asn Gly Thr Val Val Gln
                340                 345                 350

Arg His Pro Thr His Ala Val Thr Phe Val Asp Asn His Asp Ser Gln
        355                 360                 365

Pro Glu Glu Ala Leu Glu Ser Phe Val Glu Glu Trp Phe Lys Pro Leu
370                 375                 380

Ala Tyr Ala Leu Thr Leu Thr Arg Asp Gln Gly Tyr Pro Ser Val Phe
385                 390                 395                 400

Tyr Gly Asp Tyr Tyr Gly Ile Pro Thr His Gly Val Pro Ala Met Lys
                405                 410                 415

Ser Lys Ile Asp Pro Ile Leu Glu Ala Arg Gln Lys Tyr Ala Tyr Gly
                420                 425                 430

Lys Gln Asn Asp Tyr Leu Asp His His Asn Met Ile Gly Trp Thr Arg
        435                 440                 445

Glu Gly Asn Thr Ala His Pro Asn Ser Gly Leu Ala Thr Ile Met Ser
450                 455                 460

Asp Gly Pro Gly Gly Asn Lys Trp Met Tyr Val Gly Arg Asn Lys Ala
465                 470                 475                 480

Gly Gln Val Trp Arg Asp Ile Thr Gly Asn Arg Ser Gly Thr Val Thr
                485                 490                 495

Ile Asn Ala Asp Gly Trp Gly Asn Phe Ser Val Asn Gly Gly Ser Val
                500                 505                 510

Ser Ile Trp Val Asn
        515

<210> SEQ ID NO 9
<211> LENGTH: 35
<212> TYPE: DNA
<213> ORGANISM: Artificial

```
<220> FEATURE:
<223> OTHER INFORMATION: synthetic

<400> SEQUENCE: 9
tggaatctcg aggttttatc ctttaccttg tctcc                              35

<210> SEQ ID NO 10
<211> LENGTH: 103
<212> TYPE: DNA
<213> ORGANISM: Artificial
<220> FEATURE:
<223> OTHER INFORMATION: synthetic

<400> SEQUENCE: 10
cccccgctcg aggcttttct tttggaagaa aatataggga aaatggtact tgttaaaaat   60
tcggaatatt tatacaatat catatgtttc acattgaaag ggg                    103

<210> SEQ ID NO 11
<211> LENGTH: 26
<212> TYPE: DNA
<213> ORGANISM: Artificial
<220> FEATURE:
<223> OTHER INFORMATION: synthetic primer

<400> SEQUENCE: 11
accattggaa ccgcctgcgc agcgat                                       26

<210> SEQ ID NO 12
<211> LENGTH: 26
<212> TYPE: DNA
<213> ORGANISM: Artificial
<220> FEATURE:
<223> OTHER INFORMATION: synthetic primer

<400> SEQUENCE: 12
caggttgctc gcatcgctgc gcaggc                                       26

<210> SEQ ID NO 13
<211> LENGTH: 26
<212> TYPE: DNA
<213> ORGANISM: Artificial
<220> FEATURE:
<223> OTHER INFORMATION: synthetic primer

<400> SEQUENCE: 13
gatgcgagca acctgaaaga taaagg                                       26

<210> SEQ ID NO 14
<211> LENGTH: 29
<212> TYPE: DNA
<213> ORGANISM: Artificial
<220> FEATURE:
<223> OTHER INFORMATION: synthetic primer

<400> SEQUENCE: 14
actgctgtga tgcctttatc tttcaggtt                                    29

<210> SEQ ID NO 15
<211> LENGTH: 28
<212> TYPE: DNA
<213> ORGANISM: Artificial
<220> FEATURE:
<223> OTHER INFORMATION: synthetic primer

<400> SEQUENCE: 15
gattgggatc aaagccgcca gctgaaca                                     28
```

```
<210> SEQ ID NO 16
<211> LENGTH: 27
<212> TYPE: DNA
<213> ORGANISM: Artificial
<220> FEATURE:
<223> OTHER INFORMATION: synthetic primer

<400> SEQUENCE: 16
agatgcggtt gttcagctgg cggcttt                                              27

<210> SEQ ID NO 17
<211> LENGTH: 27
<212> TYPE: DNA
<213> ORGANISM: Artificial
<220> FEATURE:
<223> OTHER INFORMATION: synthetic primer

<400> SEQUENCE: 17
atctataaat ttcgcggcga tggcaaa                                              27

<210> SEQ ID NO 18
<211> LENGTH: 27
<212> TYPE: DNA
<213> ORGANISM: Artificial
<220> FEATURE:
<223> OTHER INFORMATION: synthetic primer

<400> SEQUENCE: 18
caatcccatg ctttgccatc gccgcga                                              27

<210> SEQ ID NO 19
<211> LENGTH: 27
<212> TYPE: DNA
<213> ORGANISM: Artificial
<220> FEATURE:
<223> OTHER INFORMATION: synthetic primer

<400> SEQUENCE: 19
tggatcaatc atgtcagaaa cgcgacg                                              27

<210> SEQ ID NO 20
<211> LENGTH: 27
<212> TYPE: DNA
<213> ORGANISM: Artificial
<220> FEATURE:
<223> OTHER INFORMATION: synthetic primer

<400> SEQUENCE: 20 catattttg cccgtcgcgt ttctgac                                               27

<210> SEQ ID NO 21
<211> LENGTH: 28
<212> TYPE: DNA
<213> ORGANISM: Artificial
<220> FEATURE:
<223> OTHER INFORMATION: synthetic primer

<400> SEQUENCE: 21
caatcatgtc agaagcacga cgggcaaa                                             28

<210> SEQ ID NO 22
<211> LENGTH: 27
<212> TYPE: DNA
<213> ORGANISM: Artificial
<220> FEATURE:
<223> OTHER INFORMATION: synthetic primer
```

-continued

<400> SEQUENCE: 22 catattttg cccgtcgtgc ttctgac                                    27

<210> SEQ ID NO 23
<211> LENGTH: 25
<212> TYPE: DNA
<213> ORGANISM: Artificial
<220> FEATURE:
<223> OTHER INFORMATION: synthetic primer

<400> SEQUENCE: 23
gcaagttcac catgcagtgt gtgac                                     25

<210> SEQ ID NO 24
<211> LENGTH: 25
<212> TYPE: DNA
<213> ORGANISM: Artificial
<220> FEATURE:
<223> OTHER INFORMATION: synthetic primer

<400> SEQUENCE: 24
tatcaagctt atcgataccg tcgac                                     25

<210> SEQ ID NO 25
<211> LENGTH: 22
<212> TYPE: DNA
<213> ORGANISM: Artificial
<220> FEATURE:
<223> OTHER INFORMATION: synthetic primer

<400> SEQUENCE: 25
cgattgtgag gagtggcttg tg                                        22

<210> SEQ ID NO 26
<211> LENGTH: 22
<212> TYPE: DNA
<213> ORGANISM: Artificial
<220> FEATURE:
<223> OTHER INFORMATION: synthetic primer

<400> SEQUENCE: 26
cttatcgata ccgtcgaccc tc                                        22

<210> SEQ ID NO 27
<211> LENGTH: 484
<212> TYPE: PRT
<213> ORGANISM: Bacillus sp.

<400> SEQUENCE: 27

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp

-continued

```
                100             105             110
Ala Thr Glu Met Val Arg Ala Val Glu Val Asn Pro Asn Asn Arg Asn
            115             120             125
Gln Glu Val Thr Gly Glu Tyr Thr Ile Glu Ala Trp Thr Arg Phe Asp
        130             135             140
Phe Pro Gly Arg Gly Asn Thr His Ser Ser Phe Lys Trp Arg Trp Tyr
145             150             155             160
His Phe Asp Gly Val Asp Trp Asp Gln Ser Arg Arg Leu Asn Asn Arg
                165             170             175
Ile Tyr Lys Phe Arg Gly His Gly Lys Ala Trp Asp Trp Glu Val Asp
            180             185             190
Thr Glu Asn Gly Asn Tyr Asp Tyr Leu Met Tyr Ala Asp Ile Asp Met
        195             200             205
Asp His Pro Glu Val Val Asn Glu Leu Arg Asn Trp Gly Val Trp Tyr
        210             215             220
Thr Asn Thr Leu Gly Leu Asp Gly Phe Arg Ile Asp Ala Val Lys His
225             230             235             240
Ile Lys Tyr Ser Phe Thr Arg Asp Trp Ile Asn His Val Arg Ser Ala
            245             250             255
Thr Gly Lys Asn Met Phe Ala Val Ala Glu Phe Trp Lys Asn Asp Leu
        260             265             270
Gly Ala Ile Glu Asn Tyr Leu Gln Lys Thr Asn Trp Asn His Ser Val
            275             280             285
Phe Asp Val Pro Leu His Tyr Asn Leu Tyr Asn Ala Ser Lys Ser Gly
        290             295             300
Gly Asn Tyr Asp Met Arg Asn Ile Phe Asn Gly Thr Val Val Gln Arg
305             310             315             320
His Pro Ser His Ala Val Thr Phe Val Asp Asn His Asp Ser Gln Pro
                325             330             335
Glu Glu Ala Leu Glu Ser Phe Val Glu Glu Trp Phe Lys Pro Leu Ala
            340             345             350
Tyr Ala Leu Thr Leu Thr Arg Glu Gln Gly Tyr Pro Ser Val Phe Tyr
        355             360             365
Gly Asp Tyr Tyr Gly Ile Pro Thr His Gly Val Pro Ala Met Arg Ser
370             375             380
Lys Ile Asp Pro Ile Leu Glu Ala Arg Gln Lys Tyr Ala Tyr Gly Lys
385             390             395             400
Gln Asn Asp Tyr Leu Asp His His Asn Ile Ile Gly Trp Thr Arg Glu
            405             410             415
Gly Asn Thr Ala His Pro Asn Ser Gly Leu Ala Thr Ile Met Ser Asp
        420             425             430
Gly Ala Gly Gly Ser Lys Trp Met Phe Val Gly Arg Asn Lys Ala Gly
            435             440             445
Gln Val Trp Ser Asp Ile Thr Gly Asn Arg Thr Gly Thr Val Thr Ile
        450             455             460
Asn Ala Asp Gly Trp Gly Asn Phe Ser Val Asn Gly Gly Ser Val Ser
465             470             475             480
Ile Trp Val Asn
```